United States Patent
Tsushima et al.

(10) Patent No.: US 6,790,854 B2
(45) Date of Patent: Sep. 14, 2004

(54) DIPHENYLALKYLAMINE DERIVATIVES USEFUL AS OPIOID RECEPTOR AGONISTS

(75) Inventors: Masaki Tsushima, Kanagawa (JP); Kaori Tadauchi, Kanagawa (JP); Kenji Asai, Tokyo (JP); Naoko Miike, Kanagawa (JP); Toshiaki Kudo, Kanagawa (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 57 days.

(21) Appl. No.: 10/221,172

(22) PCT Filed: Mar. 22, 2001

(86) PCT No.: PCT/JP01/02265
§ 371 (c)(1),
(2), (4) Date: Mar. 13, 2003

(87) PCT Pub. No.: WO01/70689
PCT Pub. Date: Sep. 27, 2001

(65) Prior Publication Data
US 2003/0176693 A1 Sep. 18, 2003

(30) Foreign Application Priority Data
Mar. 24, 2000 (JP) ........................................ 2000-085202

(51) Int. Cl.[7] ..................... A61K 31/438; C07D 471/10
(52) U.S. Cl. ........................... 514/278; 546/18; 546/20; 546/199; 546/201; 546/247; 514/322; 514/323; 514/331
(58) Field of Search ............................... 514/278, 322, 514/323, 331; 546/18, 20, 199, 201, 247

(56) References Cited

U.S. PATENT DOCUMENTS

| | | | |
|---|---|---|---|
| 3,196,157 A | 7/1965 | Janssen | |
| 5,559,269 A | 9/1996 | Johansson et al. | |
| 5,574,159 A | 11/1996 | Chang et al. | |
| 5,658,908 A | 8/1997 | Chang et al. | |
| 5,681,830 A | 10/1997 | Chang et al. | |
| 5,854,249 A | 12/1998 | Chang et al. | |
| 5,922,887 A | 7/1999 | Dondio et al. | |
| 6,153,626 A | 11/2000 | Pelcman et al. | |
| 6,187,792 B1 | 2/2001 | Delorme et al. | |
| 6,262,104 B1 | 7/2001 | Dondio et al. | |
| 6,313,132 B1 | 11/2001 | Johansson et al. | |
| 6,399,635 B1 | 6/2002 | Pelcman et al. | |

FOREIGN PATENT DOCUMENTS

| | | |
|---|---|---|
| WO | 93/15062 | 8/1993 |
| WO | 94/11337 | 5/1994 |
| WO | 96/36620 | 11/1996 |
| WO | 97/10230 | 3/1997 |
| WO | 97/44329 | 11/1997 |
| WO | 98/28270 | 7/1998 |
| WO | 98/28275 | 7/1998 |
| WO | 98/43942 | 10/1998 |

OTHER PUBLICATIONS

C. J. Evans et al., Science, 1992, vol. 258, pp. 1952–1955.
B. L. Kieffer et al., Proc. Natl. Acad. Sci. USA, 1992, vol. 89, pp. 12048–12052.
D. E. Moulin et al., Pain, 1985, 23, pp. 213–221.
J. J. Galligan et al., J. Pharm. Exp. Ther., 1984, vol. 229, pp. 641–648.
G. Dondio et al., Exp. Opin. Ther. Patents, 1999, 9, pp. 353–374.
S. N. Calderon et al., J. Med. Chem., 1994, 37, pp. 2125–2128.
K. Freter, J. Org. Chem., 1975, vol. 40, pp. 2525–2529.
D. Beck et al., Helv. Chim. Acta, 1968, vol. 51, pp. 260–264.

*Primary Examiner*—Charanjit S. Aulakh
(74) *Attorney, Agent, or Firm*—Greenblum & Bernstein, P.L.C.

(57) ABSTRACT

A substance having affinity for an opioid δ receptor, which is represented by the following general formula (I):

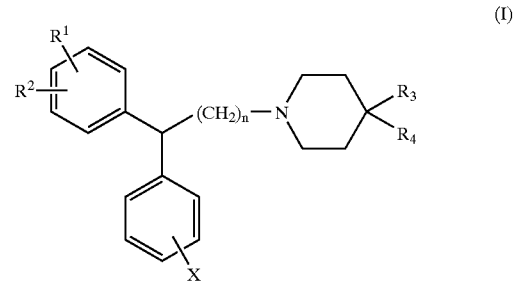

wherein, X represents a group of the general formula: —CO—N($R^5$)($R^6$) (II) and the like, n represents 1 to 3, $R^1$ and $R^2$ represent a hydrogen atom, a halogen atom, a lower alkyl group and the like, $R^3$ represents a hydrogen atom, a halogen atom, a lower alkyl group and the like, $R^4$ represents a saturated or unsaturated monocyclic or bicyclic carbocyclic group and the like, $R^5$ to $R^{12}$ represent a hydrogen atom, a lower alkyl group and the like, and $R^3$ and $R^4$, $R^5$ and $R^6$, $R^7$ or $R^8$ and $R^9$ and $R^{10}$ may bind to each other to form a cyclic structure, and a medicament useful for preventive and/or therapeutic treatment of central nervous system diseases and peripheral nervous system diseases comprising the substance as an active ingredient.

20 Claims, No Drawings

DIPHENYLALKYLAMINE DERIVATIVES USEFUL AS OPIOID RECEPTOR AGONISTS

TECHNICAL FIELD

The present invention relates to diphenylalkylamine derivatives, which have affinity for the opioid δ receptor and are useful in the medicinal field, and relates to medicaments comprising said compounds as an active ingredient.

BACKGROUND ART

Opioid receptors are mainly classified into three types, i.e., μ, δ and κ from a viewpoint of differences in pharmacological actions. On the basis of the discovery of an endogenous opioid peptide in 1970's, some progresses were made in studies about their mechanism of action. In 1990's, studies about opioid receptor structures advanced based on genetic analysis, and their mechanism of action has been being elucidated by the molecular biology. As also for the δ receptor, based on the success of cloning of δ receptor by Evans, Kieffer et al. in 1992, many studies have been vigorously performed in the medicinal and pharmaceutical fields by the molecular biology.

Although higher order functions of the opioid δ receptors have not yet been successfully elucidated, those already reported include that an opioid δ receptor agonist exhibits analgesic activity (D. E. Moulin et al., Pain, 1985, 23, 213), and that the opioid δ receptor agonist has a reducing effect on adverse reactions induced by an opioid μ receptor agonist and an opioid κ receptor agonist (Gallingan et. al., J. Pharm. Exp. Ther. 1984, 229, 641). Since the opioid δ receptor is known to be present widely in the central and peripheral nerve systems and considered to have a wide variety of functions, discovery of an effective and selective opioid δ receptor ligands can greatly contribute to therapeutic treatments of central nerve system diseases including schizophrenia, depression, cerebral apoplexy, epilepsy, Alzheimer's disease, and Parkinson's disease, and peripheral nerve system diseases including pains (Exp. Opin. ther. Patents, 1999, 9, 353).

Compounds related to the general formula (I) of the present invention are reported in J. Med. Chem. 1994, 37, 2125, WO93/15062, WO96/36620, WO97/10230, WO98/28270, WO98/28275 and the like. The compounds described in J. Med. Chem. 1994, 37, 2125 and WO93/15062 have very high affinity for δ receptors. However, these compounds have not been used clinically, because their productions are difficult due to three asymmetric centers, which are apparent from their chemical formulas, and they have poor pharmacokinetics. Derivatives having a structure with no asymmetric center are reported in WO96/36620, WO97/10230, WO98/28270, WO98/28275 and the like. However, their affinities for the δ receptor are undesirably lowered compared to the compounds described above. Thus, no compound has been reported which has a structure with no asymmetric center and high affinity for the δ receptor.

Further, among the compounds relevant to the compounds of the general formula (I) of the present invention, derivatives that do not have a partial structure represented by X have been reported in WO94/11337, WO97/44329, WO98/43942 and the like. However, as for these compounds, affinity for δ receptor has not been reported.

DISCLOSURE OF THE INVENTION

An aim of the present invention is to provide a substance having affinity for the opioid δ receptor, in particular, to provide an effective and selective opioid δ receptor ligand. A further aim is to provide a medicament useful for preventive and/or therapeutic treatment of central nerve system diseases and peripheral nerve system diseases on the basis of the features.

In the specification, the term "opioid δ receptor ligand" means a compound having an ability to bind to an opioid δ receptor, and comprehensively includes an agonist, antagonist, partial agonist, and inverse agonist for an opioid δ receptor.

In order to achieve the aim described above, the inventors of the present invention studied variety of compounds. As a result, they found that compounds represented by the following general formula (I) had high affinity for the opioid δ receptor, and achieved the present invention.

The present invention thus provides compounds represented by the following general formula (I):

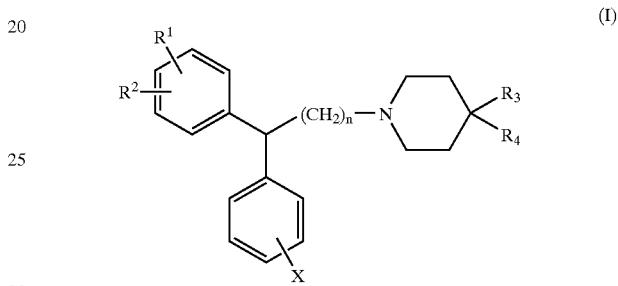

[in the formula, X represents the following group (II), (III), (IV), (V), or (VI),

n represents 1, 2 or 3, $R^1$ and $R^2$ each independently represent a hydrogen atom, a halogen atom, a lower alkyl group which may be substituted, a lower alkenyl group which may be substituted, a lower alkoxy group which may be substituted, or a hydroxy group, or represent —O—CH$_2$—O— as —$R^1$—$R^2$—, $R^3$ represents a hydrogen atom, a halogen atom, a lower alkyl group which may be substituted, a lower alkenyl group which may be substituted, a lower alkoxy group which may be substituted, a hydroxy group, a cyano group, an amino group which may be substituted, a carbamoyl group which may be substituted, a carboxyl group, a (substituted or unsubstituted lower alkoxy) carbonyl group, or a (substituted or unsubstituted lower alkyl)carbonyl group, $R^4$ represents a saturated or unsaturated monocyclic or bicyclic carbocyclic group or a monocyclic or bicyclic heterocyclic group containing one or more hetero atoms selected from the group consisting of an oxygen atom, a nitrogen atom, and a sulfur atom, $R^5$, $R^6$, $R^7$, $R^8$, $R^9$, $R^{10}$, $R^{11}$ and $R^{12}$ each independently represent a hydrogen atom, a lower alkyl group which may be substituted, or a lower alkenyl group which may be substituted, and $R^3$ and $R^4$, $R^5$ and $R^6$, $R^7$ and $R^8$, and $R^9$ and $R^{10}$ may bind to each other to form a cyclic structure] or salts thereof.

The present invention further provides medicaments comprising a substance selected from the group consisting of the compounds represented by the general formula (I) and pharmacologically acceptable salts thereof as an active ingredient. The preferred medicaments consist of a pharmaceutical composition comprising the substance described above and an additive for pharmaceutical preparations. These medicaments are useful for preventive treatment and/or therapeutic treatment of central nerve system diseases or peripheral nerve system diseases.

The present invention further provides an opioid δ receptor ligand comprising a substance selected from the group consisting of the compounds represented by the general formula (I) and pharmacologically acceptable salts thereof.

The present invention still further provides use of substances selected from the group consisting of the compounds represented by the general formula (I) and pharmacologically acceptable salts thereof for manufacture of the medicaments and methods for preventive treatment and/or therapeutic treatment of central nerve system diseases or peripheral nerve system diseases, which comprises the step of administering a preventively and/or therapeutically effective amount of a substance selected from the group consisting of the compounds represented by the general formula (I) and pharmacologically acceptable salts thereof to a mammal including human.

BEST MODE FOR CARRYING OUT THE INVENTION

The entire disclosures of Japanese Patent Application No. 2000-085202 are incorporated by reference in the disclosures of the specification.

Novel compounds of the present invention will be explained in more detail.

In the specification, a "lower alkyl group" or a "lower alkoxy group" as a substituent, or a "lower alkyl group" or "lower alkoxy group" constituting a part of a substituent means an alkyl or alkoxy group in a straight or branched chain, cyclic form, or any combination thereof having 1 to 6 carbon atoms, preferably 1 to 4 carbon atoms. Examples thereof include methyl, ethyl, n-propyl, isopropyl, cyclopropyl, n-butyl, i-butyl, s-butyl, t-butyl, n-pentyl, cyclopentyl, n-hexyl, cyclohexyl, methoxy, ethoxy, n-propoxy, isopropoxy, cyclopropoxy, n-butoxy, i-butoxy, s-butoxy, t-butoxy and the like. Similarly, a "lower alkenyl group" as a substituent means a straight, branched, or cyclic alkenyl group having 2 to 6 carbon atoms, preferably 2 to 4 carbon atoms, and examples thereof include vinyl group, allyl group and the like. In a group containing an alkenyl moiety, the number of double bonds contained in the alkenyl moiety is not particularly limited, and a double bond contained in the alkenyl moiety may either be in Z- or E-configuration.

The term "halogen atom" means a fluorine atom, chlorine atom, bromine atom, or iodine atom unless otherwise specifically mentioned.

The term "hetero atom" means, for example, a hetero atom such as an oxygen atom, nitrogen atom, or sulfur atom unless otherwise specifically mentioned, preferably an oxygen atom, nitrogen atom, or sulfur atom. A "heterocyclic ring" may contain two or more hetero atoms as ring-constituting atoms. In such compounds, two or more hetero atoms may be the same or different. A heterocyclic group means a residue of a heterocyclic ring obtained by removing one or more hydrogen atoms that bind to ring-constituting atoms.

In the formula (I), $R^5$ and $R^6$ in the group (II), $R^7$ and $R^8$ in the group (III), and $R^9$ and $R^{10}$ in the group (TV), which groups are represented by X, may each independently bind to each other to form a cyclic structure. Examples of the ring include aziridine, azetidine, pyrrolidine, or piperidine, and an example of a preferred ring includes piperidine. An unsaturated bond may exist in a part of these rings.

Further, $R^5$, $R^6$, $R^7$, $R^8$, $R^9$, $R^{10}$, $R^{11}$, and $R^{12}$ in the group (II), (III), (IV), (V), or (VI) represented by X preferably each independently represent a hydrogen atom or a lower alkyl group, or $R^5$ and $R^6$ preferably bind to each other to form piperidine. The group represented by X is preferably the group (II).

The integer represented by n is preferably 2 or 3.

$R^1$ and $R^2$ preferably represent a hydrogen atom, a halogen atom, a lower alkoxy group, or a hydroxy group, or represent —O—$CH_2$—O— as —$R^1$—$R^2$—. $R^1$ and $R^2$ most preferably represent a hydrogen atom, a fluorine atom, a methoxy group, or a hydroxy group.

$R^3$ is preferably a hydrogen atom or a lower alkylcarbonyl group, and most preferably a hydrogen atom.

Examples of the carbocyclic ring constituting the saturated or unsaturated monocyclic or bicyclic carbocyclic group represented by $R^4$ include rings of cyclopentane, cyclohexane, benzene, indane, naphthalene and the like, and a preferred example includes benzene.

Examples of the heterocyclic ring constituting the monocyclic or bicyclic heterocyclic group containing one or more hetero atoms represented by $R^4$ include rings of imidazole, benzofuran, indole, benzothiophene, benzothiazole, benzoxazole, benzimidazole, benzotriazole, benzisothiazole, benzisoxazole, quinoline, isoquinoline, quinazoline, pyridinoimidazole, benzoxazine and the like, and preferred examples include indole and benzimidazole.

An unsaturated bond as a part of the saturated or unsaturated monocyclic or bicyclic carbocyclic group or the monocyclic or bicyclic heterocyclic ring containing one or more hetero atoms represented by $R^4$ may be hydrogenated to form a saturated bond, or may be oxidized to form a cyclic ketone, cyclic amide (lactam), cyclic ester (lactone) or cyclic ureide structure. A substituting position of the adjacent piperidine ring may be any substitutable position.

One or more hydrogen atoms on the saturated or unsaturated monocyclic or bicyclic carbocyclic group or the monocyclic or bicyclic heterocyclic ring containing one or more hetero atoms represented by $R^4$ may be substituted. Examples of the substituent include a lower alkyl group such as methyl group, a lower alkoxy group such as methoxy group, a lower alkenyl group such as allyl group, a halogen atom, a hydroxy group, a cyano group, an amino group, a N-(lower alkyl)amino group such as N-methylamino group, a N,N-di(lower alkyl)amino group such as N,N-dimethylamino group, a nitro group, a carbamoyl group, a N-(lower alkyl)carbamoyl group such as N-methylcarbamoyl group, a N,N-di(lower alkyl)carbamoyl group such as N,N-dimethylcarbamoyl group, a carboxyl group, a lower alkoxycarbonyl group such as methoxycarbonyl group, a lower alkylcarbonyl group such as acetyl group, an oxo group, a benzyl group, a hydroxymethyl group and the like. Preferred substituents are a lower alkyl group, an oxo group, a benzyl group, and a hydroxymethyl group, and particularly preferred substituents are a lower alkyl group, an oxo group, and hydroxymethyl group. When two or more substituents exist, they may be the same or different. Positions of substituents are not limited, and they can exist at any substitutable positions.

Further, an example of the compounds wherein $R^5$ and $R^6$ bind to each other to form a cyclic structure include the compounds in which a spiro ring is formed. Specifically, examples include the following groups (VII) and (VII) (In the following chemical formulas, a spiro ring is formed in each upper ring. In the formulas, each of two solid lines drawn from a ring represents a single bond that binds to the 3- or 5-position of the piperidine ring on which $R^3$ and $R^4$ substitute).

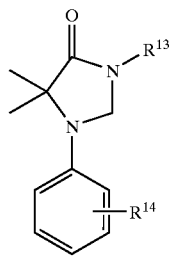

(VII)

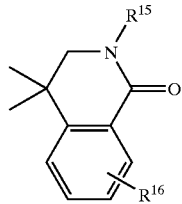

(VIII)

[in the groups, $R^{13}$ and $R^{15}$ each independently represent a hydrogen atom, a lower alkyl group which may be substituted, or a lower alkenyl group which may be substituted, and $R^{14}$ and $R^{16}$ each independently represent a hydrogen atom, a halogen atom, a substituted or unsubstituted lower alkyl group, a lower alkenyl group which may be substituted, a lower alkoxy group which may be substituted, a hydroxy group, a cyano group, an amino group which may be substituted, a nitro group, a carbamoyl group which may be substituted, a carboxyl group, a (substituted or unsubstituted lower alkoxy) carbonyl group, or (substituted or a unsubstituted lower alkyl)carbonyl group]

The definition that a group represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ or $R^{16}$ "may be substituted" means that the group may have any kind of one or more of substituents. When the groups have two or more substituents, they may be the same or different. The positions of the substituents are not limited, and they can exist at any substitutable positions. Kinds of the substituents are not limited, and examples include a lower alkyl group such as methyl group, a lower alkoxy group such as methoxy group, a lower alkenyl group such as allyl group, a halogen atom, a hydroxy group, a cyano group, an amino group, a N-(lower alkyl)amino group such as N-methylamino group, a N,N-di(lower alkyl)amino group such as N,N-dimethylamino group, a nitro group, a carbamoyl group, a N-(lower alkyl)carbamoyl group such as N-methylcarbamoyl group, a N,N-di(lower alkyl)carbamoyl group such as N,N-dimethylcarbamoyl group, a carboxyl group, a (lower alkoxy)carbonyl group such as methoxycarbonyl group, a (lower alkyl)carbonyl group such as acetyl group, and a saturated or unsaturated 3- to 6-membered carbocyclic group such as cyclopropyl, cyclopentyl, cyclohexyl and phenyl (these carbocyclic groups may have one or more substituents, and examples of the substituents include a lower alkyl group such as methyl group, a lower alkoxy group such as methoxy group, a lower alkenyl group such as allyl group, a halogen atom, a hydroxy group, a cyano group, an amino group, a N-(lower alkyl)amino group such as N-methylamino group, a N,N-di(lower alkyl)amino group such as N,N-dimethylamino group, a nitro group, a carbamoyl group, a N-(lower alkyl)carbamoyl group such as N-methylcarbamoyl group, a N,N-di(lower alkyl)carbamoyl group such as N,N-dimethylcarbamoyl group, a carboxyl group, a (lower alkoxy)carbonyl group such as methoxycarbonyl group, a (lower alkyl)carbonyl group such as acetyl group and the like), and a phenyl group is preferred.

Among the compounds represented by the general formula (I), examples of preferred class of compounds include those wherein $R^4$ represents a residue of a ring selected from a group consisting of benzene, indole, and benzimidazole (a part of unsaturated bonds of the ring may be hydrogenated to form a saturated bond(s), or the ring may be substituted).

Another preferred class of compounds include those wherein $R^3$ and $R^4$ form a cyclic structure and represent the following group (VII) or (VIII):

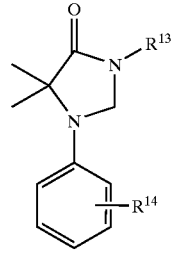

(VII)

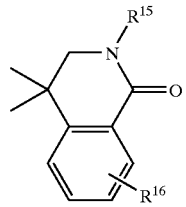

(VIII)

[in the groups, $R^{13}$, $R^{15}$, $R^{14}$ and $R^{16}$ have the same meanings as defined above].

More preferred class of compounds include those wherein X represents the group (II), (III), (IV), (V) or (VI), n is 2 or 3, $R^1$ and $R^2$ each independently represent a hydrogen atom, a halogen atom, a lower alkoxy group, or a hydroxy group, or $R^1$ and $R^2$ represent —O—CH$_2$—O— as —$R^1$—$R^2$—, R³ is a hydrogen atom or a lower alkylcarbonyl group, R⁴ is a residue of a ring selected from the group consisting of benzene, indole, and benzimidazole (a part of unsaturated bonds of the ring may be hydrogenated to form a saturated bond(s), and a hydrogen atom on the ring may be substituted with an oxo group, a lower alkyl group, a hydroxymethyl group, or a benzyl group), or R³ and R⁴ bind to each other to form a cyclic structure of a ring selected from imidazole, N-phenylimidazolidine, and isoquinoline (a hydrogen atom on the ring may be substituted with an oxo group or a lower alkyl group), and $R^5$, $R^6$, $R^7$, $R^8$, $R^9$, $R^{10}$, $R^{11}$, and $R^{12}$ each independently represent a hydrogen atom or a lower alkyl group, or $R^5$ and $R^6$ bind to each other to form piperidine.

Further preferred class of compounds include those wherein X represents the group (II).

In the present invention, among the compounds represented by the general formula (I), particularly preferred compounds are as follows.

1. 1-[3-(4-Diethylcarbamoylphenyl)-3-(3-methoxyphenyl)propyl]-4-(1,3-dihydro-2H-benzimidazol-2-on-1-yl)piperidine
2. 1-[3-(4-Diethylcarbamoylphenyl)-3-(3-hydroxyphenyl)propyl]-4-(1,3-dihydro-2H-benzimidazol-2-on-1-yl)piperidine hydrochloride
3. 8-[3-(4-Diethylcarbamoylphenyl)-3-(3-methoxyphenyl)propyl]-1-phenyl-1,3,8-triazaspiro[4,5]decan-4-one
4. 1-[3-(4-Diethylcarbamoylphenyl)-3-(3-methoxyphenyl)propyl]-4-(2-hydroxymethyl-1H-benzimidazol-1-yl)piperidine
5. 1'-[3-(4-Diethylcarbamoylphenyl)-3-(3-methoxyphenyl)propyl]-2,3-dihydro-5-methylspiro[isoquinoline-4(1H),4'-piperidin]-1-one
6. 1'-[3-(4-Diethylcarbamoylphenyl)-3-(3-hydroxyphenyl)propyl]-2,3-dihydro-5-methylspiro[isoquinoline-4(1H),4'-piperidin]-1-one hydrochloride
7. 1-[3-(4-Diethylcarbamoylphenyl)-3-(2-methoxyphenyl)propyl]-4-(1,3-dihydro-2H-benzimidazol-2-on-1-yl)piperidine
8. 8-[3-(4-Diethylcarbamoylphenyl)-3-(2-methoxyphenyl)propyl]-1-phenyl-1,3,8-triazaspiro[4,5]decan-4-one
9. 1'-[3-(4-Diethylcarbamoylphenyl)-3-(2-methoxyphenyl)propyl]-2,3-dihydro-5-methylspiro[isoquinoline-4(1H),4'-piperidin]-1-one
10. 1-[3-(4-Diethylcarbamoylphenyl)-3-(2-methoxyphenyl)propyl]-4-(2-hydroxymethyl-1H-benzimidazol-1-yl)piperidine
11. 1-[3-(4-Diethylcarbamoylphenyl)-3-(3-methoxyphenyl)propyl]-4-(1H-benzimidazol-1-yl)piperidine
12. 1-[3-(4-Diethylcarbamoylphenyl)-3-(4-methoxyphenyl)propyl]-4-(1,3-dihydro-2H-benzimidazol-2-on-1-yl)piperidine
13. 1-[3-(4-Diethylcarbamoylphenyl)-3-(4-hydroxyphenyl)propyl]-4-(1,3-dihydro-2H-benzimidazol-2-on-1-yl)piperidine hydrochloride
14. 1-[3-(4-Diethylcarbamoylphenyl)-3-(3-methoxyphenyl)propyl]-4-(2-methyl-1H-benzimidazol-1-yl)piperidine
15. 1-[3-(4-Diethylcarbamoylphenyl)-3-(2-hydroxyphenyl)propyl]-4-(1,3-dihydro-2H-benzimidazol-2-on-1-yl)piperidine hydrochloride
16. 1-[3-(3-Diethylcarbamoylphenyl)-3-(3-methoxyphenyl)propyl]-4-(1,3-dihydro-2H-benzimidazol-2-on-1-yl)piperidine
17. 1-[3-(4-Diethylcarbamoylphenyl)-3-(3-methoxyphenyl)propyl]-4-(3-benzyl-1,3-dihydro-2H-benzimidazol-2-on-1-yl)piperidine
18. 1-[3-(4-Diethylcarbamoylphenyl)-3-(3-methoxyphenyl)propyl]-4-(3-cyclopropylmethyl-1,3-dihydro-2H-benzimidazol-2-on-1-yl)piperidine
19. 1-[4-(4-Diethylcarbamoylphenyl)-4-(3-methoxyphenyl)butyl]-4-(1,3-dihydro-2H-benzimidazol-2-on-1-yl)piperidine
20. 1-[3-(4-Diethylcarbamoylphenyl)-3-(3-methoxyphenyl)propyl]-4-(3,3-dimethyl-2,3-dihydro-1H-indol-2-on-1-yl)piperidine
21. 1-[3-(4-Diethylcarbamoylphenyl)-3-(3-fluorophenyl)propyl]-4-(1,3-dihydro-2H-benzimidazol-2-on-1-yl)piperidine
22. 8-[3-(4-Diethylcarbamoylphenyl)-3-(3-hydroxyphenyl)propyl]-8-phenyl-1,3,8-triazaspiro[4,5]decan-4-one hydrochloride
23. 1-[3-(4-Diethylcarbamoylphenyl)-3-(1,3-benzodioxole-5-yl)propyl]-4-(1,3-dihydro-2H-benzimidazol-2-on-1-yl)piperidine
24. 1-[4-(4-Diethylcarbamoylphenyl)-4-(3-hydroxyphenyl)butyl]-4-(1,3-dihydro-2H-benzimidazol-2-on-1-yl)piperidine hydrochloride
25. 1-[3-(4-Diethylcarbamoylphenyl)-3-(3,4-dihydroxyphenyl)propyl]-4-(1,3-dihydro-2H-benzimidazol-2-on-1-yl)piperidine hydrochloride
26. 1-[3-(4-Diethylcarbamoylphenyl)-3-(3-methoxyphenyl)propyl]-4-1H-indol-3-yl)-piperidine
27. 1-[3-(4-Diethylcarbamoylphenyl)-3-(3-hydroxyphenyl)propyl]-4-(1H-indol-3-yl)-piperidine hydrochloride
28. 1-[3-(4-Diethylcarbamoylphenyl)-3-(3-hydroxyphenyl)propyl]-4-(2-hydroxymethyl-1H-benzimidazol-1-yl)piperidine hydrochloride
29. 1-[3-(4-Diethylcarbamoylphenyl)-3-phenylpropyl]-4-(1,3-dihydro-2H-benzimidazol-2-on-1-yl)piperidine
30. 1-[3-(4-Diisopropylcarbamoylphenyl)-3-(3-methoxyphenyl)propyl]-4-(1,3-dihydro-2H-benzimidazol-2-on-1-yl)piperidine
31. 1-[3-(4-Diethylcarbamoylphenyl)-3-(4-fluorophenyl)propyl]-4-(1,3-dihydro-2H-benzimidazol-2-on-1-yl)piperidine
32. 1-[3-(4-Piperidinocarbonylphenyl)-3-(3-methoxyphenyl)propyl]-4-(1,3-dihydro-2H-benzimidazol-2-on-1-yl)piperidine
33. 1-[3-(4-Diethylcarbamoylphenyl)-3-(3-hydroxyphenyl)propyl]-4-(1H-benzimidazol-1-yl)piperidine hydrochloride
34. 1-[3-(4-Carboxylphenyl)-3-(3-methoxyphenyl)propyl]-4-(1,3-dihydro-2H-benzimidazol-2-on-1-yl)piperidine hydrochloride
35. 4-(1,3-Dihydro-2H-benzimidazol-2-on-1-yl)-1-[3-(4-methoxycarboxylphenyl)-3-(3-methoxyphenyl)propyl]piperidine
36. 4-Acetyl-1-[3-(4-diethylcarbamoylphenyl)-3-(3-methoxyphenyl)propyl]-4-phenylpiperidine
37. 1'-[3-(4-Diethylaminosulfonylphenyl)-3-(3-methoxyphenyl)propyl]-2,3-dihydro-5-methylspiro[isoquinoline-4(1H),4'-piperidin]-1-one 38. 2,3-Dihydro-5-methyl-1'-[3-[4-(1-methylbutyryl)phenyl]-3-(3-methoxyphenyl)-propyl]spiro[isoquinoline-4(1H),4'-piperidin]-1-one
39. 1-[3-(4-Diethylaminomethylphenyl)-3-(3-methoxyphenyl)propyl]-4-(1H-benzimidazol-1-yl)piperidine Methods for preparing the novel compounds of the present invention will be explained in more detail. The novel compounds of the present invention can be prepared by the methods described below.

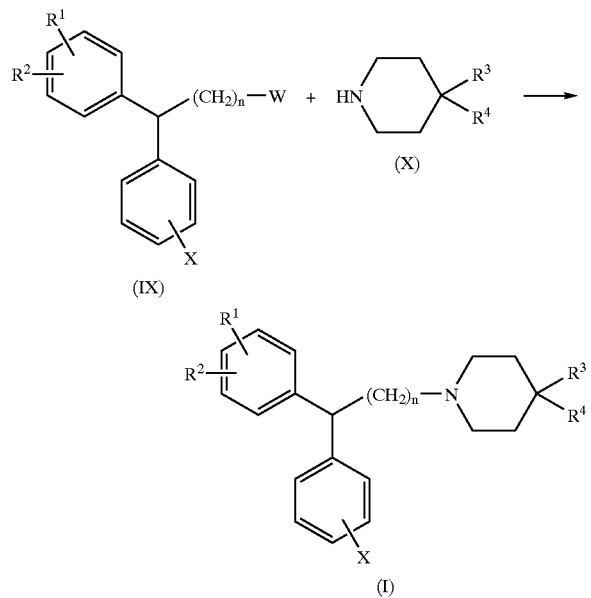

[in the formulas, $R^1$, $R^2$, $R^3$, $R^4$, X and n have the same meanings as defined in the general formula (I), and W represents a halogen atom excluding a fluorine atom or represents a leaving group such as p-toluenesulfonyloxy group, methanesulfonyloxy group, or trifluoromethanesulfonyloxy group].

The compounds (IX) can be prepared by the method described in WO97/10230 with partial modification, and a specific preparation thereof is described later in Reference Example 1.

The compounds (X) can be obtained as commercially available reagents, or can also be obtained by a known method or an improved method thereof.

The compounds (I) according to the present invention can be obtained by a reaction of a compound (IX) and a compound (X) in a solvent that is not involved in the reaction (for example, dichloromethane, tetrahydrofuran, methyl ethyl ketone, N,N-dimethylformamide, dimethyl sulfoxide and the like) in the presence of a base (for example, pyridine, triethylamine, diisopropylethylamine, 4-dimethylaminopyridine, potassium carbonate, sodium carbonate and the like) at a reaction temperature of which lower limit is 20° C. and upper limit is 100° C., preferably lower limit is 20° C. and upper limit is 50° C., for a reaction time of which lower limit is 2 hours and upper limit is 48 hours, preferably lower limit is 16 hours and upper limit is 24 hours.

In the synthesis of the compounds of the present invention, purification of a target compound from a reaction mixture is performed by methods ordinarily used in the filed of organic chemistry, for example, by distribution of reaction products between water and an organic solvent that is not freely miscible with water (e.g., benzene, toluene, ethyl acetate, butyl acetate, methyl isobutyl ketone, chloroform, dichloromethane and the like) for extraction, and then by concentration, crystallization and the like. Further, as required, fractionation purification by column chromatography using alumina, silica gel or the like, for example, may also be performed.

The compounds of the present invention may be in the form of a salt. The salt may be an acid addition salt such as salts with inorganic acids including hydrochloric acid, nitric acid, hydrobromic acid, and sulfuric acid, salts with aliphatic monocarboxylic acids, dicarboxylic acids, hydroxyalkanoic acids, hydroxydialkanoic acids, amino acids and the like, or salts deriving from non-toxic organic acids such as aromatic acids, aliphatic acids, and aromatic sulfonic acid. Examples of such acid addition salts include hydrochloride, hydrobromide, nitrate, sulfate, hydrogensulfate, hydrogenphosphate, dihydrogenphosphate, acetate, propionate, tartrate, oxalate, malonate, succinate, fumarate, maleate, mandelate, benzoate, phthalate, methanesulfonate, benzenesulfonate, toluenesulfonate, citrate, lactate, malate, glycolate, trifluoroacetate and the like.

Typical compounds of the present invention are specifically explained in detail in the examples of the present specification. Therefore, those skilled in the art can prepare any compound falling within the scope of the general formula (I) based on explanations of the general preparation methods describer above and examples described later by appropriately choosing starting compounds, reagents, reaction conditions and the like, and if necessary, applying appropriate modifications or alterations to the methods disclosed in the examples.

As well as the compounds in free form or salts thereof, any hydrates and solvates thereof also fall within the scope of the present invention. The types of solvents that form the solvates are not particularly limited. Examples include solvents such as methanol, ethanol, acetone, and diethyl ether. However, the solvents are not limited to these examples.

The compounds of the present invention may have one or more asymmetric carbon atoms depending on the type of substituent, and any of stereoisomers such as optically active isomers or diastereoisomers in a pure form, any mixtures of the stereoisomers, racemates and the like also fall within the scope of the present invention.

The compounds of the present invention are characterized to have affinity for opioid δ receptor. Therefore, the compounds of the present invention are useful for preventive and/or therapeutic treatment of central nerve system diseases such as schizophrenia, depression, cerebral apoplexy, epilepsy, Alzheimer's disease, and Parkinson's disease and peripheral nerve system diseases such as pains, in which the opioid δ receptor is involved.

The medicaments provided by the present invention are characterized to comprise at least one kind of the compound represented by the general formula (I) or pharmacologically acceptable salt thereof as an active ingredient. The medicaments of the present invention can be administered to human or animals other than human by any of oral or parenteral routes (for example, intravenous injection, intramuscular injection, subcutaneous administration, rectal administration, percutaneous administration, intraspinal administration). As the medicaments of the present invention, the substances as active ingredients, per se, may be administered. It is generally preferable to prepare and administer a pharmaceutical composition, as a form suitable for the administration route, by using one or more kinds of additives for pharmaceutical preparations.

Specifically, examples of orally available formulations include tablets, capsules, powders, granules, syrups and the like. Examples of parenteral formulations include injections such as intravenous and intramuscular injections, formulations for rectal administration, oily suppositories, aqueous suppositories and the like.

These various pharmaceutical preparations can be prepared by using additives for pharmaceutical preparations which are ordinarily used, for example, excipients, disintegrating agents, binders, lubricants and coloring agents.

Examples of the excipients include lactose, glucose, cornstarch, sorbit, crystalline cellulose and the like. Examples of the disintegrating agents include starch, sodium alginate, gelatin powder, calcium carbonate, calcium citrate, dextrin and the like. Example of the binders include dimethylcellulose, polyvinyl alcohol, polyvinyl ether, methylcellulose, ethylcellulose, gum arabic, gelatin, hydroxypropylcellulose, polyvinylpyrrolidone and the like. Examples of the lubricants include talc, magnesium stearate, polyethylene glycol, hydrogenated vegetable oil and the like. Further, the pharmaceutical preparations can be prepared with addition of a buffer, pH modifier, stabilizer or the like as required.

Although content of the compound of the present invention in the pharmaceutical composition may vary depending on types of formulations. Generally, its lower limit is about 0.1% by weight and upper limit is 50% by weigh, preferably lower limit is 0.5% by weight and upper limit is 20% by weight based on the total composition. A dose may appropriately be determined depending on each case in consideration of the age, body weight, sex, type of a disease, severity of symptoms of a patient and the like. Generally, its lower limit is 1 mg and upper limit is 1000 mg, preferably its lower limit is 1 mg and upper limit is 300 mg, per day for an adult. The dose is administered once a day or several times a day dividedly.

EXAMPLES

The present invention will be explained more specifically with reference to the following examples and test example. However, the scope of the present invention is not limited to these examples.

Reference Example 1

1-Bromo-3-(4-diethylcarbamoylphenyl)-3-(3-methoxyphenyl)-propane (a) Ethyl 3-(4-diethylcarbamoylphenyl)-3-(3-methoxyphenyl)Propionate Ethyl 3-(4-diethylcarbamoylphenyl)-3-(3-methoxyphenyl)acrylate (308 mg) synthesized by the method described in WO97/10230 was dissolved in methanol (6 ml), added with 10% palladium/carbon (60 mg) and stirred at room temperature for 22 hours under a hydrogen gas atmosphere. Insoluble solids were removed by filtration, and then the solvent was evaporated under reduced pressure to obtain 275 mg of the title compound. Yield: 89%.

$^1$H-NMR (CDCl$_3$); δ (ppm) 1.00–1.30 (9H, m), 3.02 (2H, d, J=7Hz), 3.24 (2H, br-s), 3.49 (2H, br-s), 3.77 (3H, s), 4.04 (2H, q, J=7Hz), 4.53 (1H, t, J=7Hz), 6.70–6.90 (3H, m), 7.15–7.35 (5H, m) MS (TSP); m/z 384 (MH$^+$)

(b) 3-(4-Diethylcarbamoylphenyl)-1-hydroxy-3-(3-methoxyphenyl)Propane

Ethyl 3-(4-diethylcarbamoylphenyl)-3-(3-methoxyphenyl)propionate (275 mg) was dissolved in a mixed solution of methanol (5.6 ml) and water (2.8 ml), added with 1 N aqueous sodium hydroxide (1.4 ml) and stirred at 50° C. for 1 hour. The solvent was evaporated under reduced pressure and added with 1 N aqueous hydrochloric acid (5 ml), and the reaction mixture was extracted twice with dichloromethane (5 ml). The organic layer was dried over anhydrous magnesium sulfate, and then the solvent was evaporated under reduced pressure to obtain 3-(4-diethylcarbamoylphenyl)-3-(3-methoxyphenyl) propionic acid.

The resulting 3-(4-diethylcarbamoylphenyl)-3-(3-methoxyphenyl)propionic acid was dissolved in dimethoxyethane (5.6 ml), added with triethylamine (0.12 ml) and isobutyl chloroformate (0.11 ml) under ice cooling and then the mixture was stirred at the same temperature for 30 minutes. Insoluble solids were removed by filtration, and then the filtrate was ice-cooled, added with a solution of sodium borohydride (40.7 mg) dissolved in water (1 ml) and further stirred at the same temperature for 10 minutes. The solvent was evaporated under reduced pressure and added with water (5 ml), and the reaction mixture was extracted twice with dichloromethane (5 ml). The organic layer was dried over anhydrous magnesium sulfate, and then the solvent was evaporated under reduced pressure to obtain 215 mg of the title compound. Yield: 88% (for the two steps).

$^1$H-NMR (CDCl$_3$); δ (ppm) 1.03 (3H, br-s), 1.24 (3H, br-s), 2.29 (2H, q, J=5Hz), 3.24 (2H, br-s), 3.53 (2H, br-s), 3.60 (2H, t, J=5Hz), 3.77 (3H, s), 4.14 (1H, t, J=5Hz), 6.70–6.90 (3H, m), 7.15–7.35 (5H, m) MS (TSP); m/z 342 (MH$^+$)

(c) 1-Bromo-3-(4-diethylcarbamoylphenyl)-3-(3-methoxyphenyl)Propane 3-(4-Diethylcarbamoylphenyl)-1-hydroxy-3-(3-methoxyphenyl)propane (215 mg) was dissolved in acetonitrile (4 ml), added with triphenylphosphine (304 mg) and carbon tetrabromide (385 mg) under ice cooling and stirred at room temperature for 30 minutes. The reaction mixture was added with water (5 ml) and extracted twice with dichloromethane (5 ml). The organic layer was dried over anhydrous magnesium sulfate, and then the solvent was evaporated under reduced pressure. The residue was purified by silica gel column chromatography (elution solvent: hexane: ethyl acetate=2:1) to obtain 189 mg of the title compound. Yield: 74%.

$^1$H-NMR (CDCl$_3$); δ (ppm) 1.01 (3H, br-s), 1.21 (3H, br-s), 2.55 (2H, q, J=5Hz), 3.24 (2H, br-s), 3.31 (2H, t, J=5Hz), 3.51 (2H, br-s), 3.77 (3H, s), 4.20 (1H, t, J=5Hz), 6.70–6.90 (3H, m), 7.15–7.35 (5H, m) MS (FAB); m/z 404 (MH$^+$), 406

Reference Example 2

4-(1H-Benzimidazol-1-yl)Piperidine Trifluoroacetate (a) 1-(tert-Butoxycarbonyl)-4-hydroxypiperidine 4-Hydroxypiperidine hydrochloride (3 g) was dissolved in dioxane (30 ml), added with di-tert-butyl dicarbonate (5.2 g) and stirred at room temperature for 10 minutes. The reaction mixture was added with 8% aqueous sodium hydrogencarbonate (60 ml) and further stirred for 3.5 hours. Dioxane was evaporated under reduced pressure, and the aqueous layer was extracted with ethyl acetate (60 ml). The organic layer was dried over anhydrous magnesium sulfate, and then the solvent was evaporated under reduced pressure to obtain 4.81 g of the title compound. Yield: 100%.

$^1$H-NMR (CDCl$_3$); δ (ppm) 1.46 (11H, m), 1.86 (2H, m), 3.04 (2H, m), 3.85 (3H, m)

(b) 1-(tert-Butoxycarbonyl)-4-(p-toluenesulfonyloxy) Piperidine 1-(tert-Butoxycarbonyl)-4-hydroxypiperidine (4.81 g) was dissolved in pyridine (48 ml), added with p-toluenesulfonyl chloride (9.0 g) and triethylamine (6.7 ml) and stirred at room temperature for 17 hours. The reaction mixture was added with cold water (500 ml) and stirred for 2 hours, and then the produced crystals were collected by filtration. These crystals were purified by silica gel column chromatography (elution solvent: hexane:ethyl acetate=3:1) to obtain 6.49 g of the title compound. Yield: 76%.

$^1$H-NMR (CDCl$_3$); δ (ppm) 1.43 (9H, s), 1.59 (2H, m), 1.70 (2H, m), 2.45 (3H, s), 3.25 (2H, m), 3.57 (2H, m), 4.67 (1H, m), 7.34 (2H, d, J=8Hz), 7.79 (2H, d, J=8Hz)

(c) 1-(tert-Butoxycarbonyl)-4-(1H-benzimidazol-1-yl) Piperidine $^1$H-Benzimidazole (300 mg) was dissolved in N,N-dimethylformamide (6 ml), added with sodium hydride (60%, in oil, 122 mg) and stirred at room temperature for 1 hour. Subsequently, the reaction mixture was added with 1-(tert-butoxycarbonyl)-4-(p-toluenesulfonyloxy)piperidine (1.08 g) and further stirred at room temperature for 23 hours and at 60° C. for 2 hours. The reaction mixture was added with water (10 ml) and extracted twice with ethyl acetate (10 ml). The organic layer was dried over anhydrous magnesium sulfate, and then the solvent was evaporated under reduced pressure. The residue was purified by silica gel column chromatography (elution solvent: ethyl acetate) to obtain 192 mg of the title compound. Yield: 25%.

$^1$H-NMR (CDCl$_3$); δ (ppm) 1.51 (9H, s), 2.03 (2H, m), 2.18 (2H, m), 2.94 (2H, m), 4.36 (3H, m), 7.30 (2H, m), 7.43 (1H, m), 7.82 (1H, m), 7.98 (1H, s) MS (TSP); m/z 302 (MH$^+$)

(d) 4-(1H-Benzimidazol-1-yl)Piperidine Trifluoroacetate 1-(tert-Butoxycarbonyl)-4-(1H-benzimidazol-1-yl) piperidine (192 mg) was dissolved in dichloromethane (1.9 ml), added with trifluoroacetic acid (1.9 ml) and stirred at room temperature for 1 hour. The solvent was evaporated under reduced pressure and added with diisopropyl ether, and then the produced crystals were collected by filtration to obtain 200 mg of the title compound. Yield: 100%.

$^1$H-NMR (D$_2$O); δ (ppm) 2.25 (2H, m), 2.48 (2H, m), 3.22 (2H, m), 3.59 (2H, m), 4.96 (1H, m), 7.54 (2H, m), 7.72 (1H, m), 7.80 (1H, m), 9.21 (1H, s)

Reference Example 3

2,3-Dihydro-5-methylspiro[isoquinoline-4(1H),4'-piperidin]-1-one Trifluoroacetate (a) Bis(2-hydroxyethyl)Benzylamine Bis(2-hydroxyethyl)amine (5 g) was dissolved in N,N-dimethylformamide (100 ml), added with benzyl bromide (6.52 ml) and potassium carbonate (8.657 g) and stirred at room temperature for 21 hours. The reaction mixture was added with water (200 ml) and extracted twice with dichloromethane (200 ml). The organic layer was dried over anhydrous magnesium sulfate, and then the solvent was evaporated under reduced pressure. The residue was purified by silica gel column chromatography (elution solvent: dichloromethane:methanol=20:1→10:1) to obtain 7.631 g of the title compound. Yield: 75%.

$^1$H-NMR (CDCl$_3$); δ (ppm) 2.34 (2H, br-s), 2.72 (4H, t, J=6Hz), 3.63 (4H, t, J=6Hz), 3.71 (2H, s), 7.20–7.40 (5H, m) MS (FAB); m/z 196 (MH$^+$)

(b) 1-Benzyl-4-cyano-4-(2-methylphenyl)Piperidine

Bis(2-hydroxyethyl)Benzylamine (1 g) was dissolved in dichloromethane (20 ml), added with thionyl chloride (1.9 ml) with ice cooling and stirred at room temperature for 2.5 hours. The reaction mixture was added with water (10 ml) under ice cooling, and adjusted to pH 7 with saturated aqueous sodium hydrogencarbonate. The layers were separated, and the aqueous layer was further extracted with dichloromethane (20 ml). The organic layer was dried over anhydrous magnesium sulfate, and then the solvent was evaporated under reduced pressure to obtain bis(2-chloroethyl)Benzylamine (1.090 g).

1-(2-Methylphenyl)acetonitrile (610 mg) was dissolved in dimethyl sulfoxide (6.1 ml), added with sodium hydride (60% in oil, 409 mg) and stirred at room temperature for 30 minutes. This reaction mixture was added with a solution of bis(2-chloroethyl)benzylamine (1.090 g) obtained above dissolved in dimethyl sulfoxide (6.1 ml) and further stirred at 75° C. for 2.5 hours. The reaction mixture was added with water (50 ml) and extracted twice with ether (50 ml). The organic layer was dried over anhydrous magnesium sulfate, and then the solvent was evaporated under reduced pressure. The residue was purified by silica gel column chromatography (elution solvent: hexane:ethyl acetate=6:1) to obtain 1.077 g of the title compound. Yield: 80%.

$^1$H-NMR (CDCl$_3$); δ (ppm) 2.07 (2H, td, J=12Hz, 3Hz), 2.32 (2H, dd, J=12Hz, 3Hz), 2.59 (2H, t, J=12Hz), 2.64 (3H, s), 3.01 (2H, d, J=12Hz), 3.61 (2H, s), 7.20–7.40 (9H, m) MS (TSP); m/z 291 (MH$^+$)

(c) 4-Cyano-1-(ethoxycarbonyl)-4-(2-methylphenyl) Piperidine

1-Benzyl-4-cyano-4-(2-methylphenyl)piperidine (406 mg) was dissolved in dichloromethane (8 ml), added with ethyl chloroformate (0.16 ml) and potassium hydrogencarbonate (168 mg) and stirred at room temperature for 24 hours. The reaction mixture was added with water (10 ml) and extracted twice with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=5:1→4:1) to obtain 381 mg of the title compound. Yield: 100%.

$^1$H-NMR (CDCl$_3$); δ (ppm) 1.28 (3H, t, J=7Hz), 1.92 (2H, td, J=12Hz, 3Hz), 2.34 (2H, d, J=12Hz), 2.66 (3H, s), 3.33 (2H, m), 4.16 (2H, q, J=7Hz), 4.34 (2H, m), 7.26 (4H, m) MS (EI); m/z 272 (M$^+$)

(d) 1-(Ethoxycarbonyl)-4-(ethoxycarbonylaminomethyl)-4-(2-methylphenyl)Piperidine 4-Cyano-1-(ethoxycarbonyl)-4-(2-methylphenyl) piperidine (504 mg) was dissolved in ethanol (10 ml), added with 10% palladium/carbon (500 mg) and 5 N aqueous hydrochloric acid (0.74 ml) and stirred at room temperature for 15 hours under hydrogen gas pressure (30 psi) by using Paar apparatus. Insoluble solids were removed by filtration, and then ethanol was evaporated under reduced pressure. The residue was added with dichloromethane (50 ml) and adjusted to pH 9 with saturated aqueous sodium hydrogencarbonate. The organic layer was separated, and the aqueous layer was further extracted with dichloromethane (50 ml). The organic layer was dried over anhydrous magnesium sulfate, and then the solvent was evaporated under reduced pressure to obtain 4-aminomethyl-1-(ethoxycarbonyl)-4-(2-methylphenyl)piperidine.

Subsequently, the obtained 4-aminomethyl-1-(ethoxycarbonyl)-4-(2-methylphenyl)piperidine was dissolved in dichloromethane (10 ml), added with ethyl chloroformate (0.18 ml) and triethylamine (0.26 ml) and stirred at room temperature for 30 minutes. The reaction mixture was added with water (10 ml), and the layers were separated. Then, the aqueous layer was further extracted with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=2:1) to obtain 372 mg of the title compound. Yield: 51% (for the two steps).

¹H-NMR (CDCl₃); δ (ppm) 1.10–1.30 (6H, m), 1.85 (2H, m), 2.31 (2H, m), 2.51 (3H, s), 3.26 (2H, m), 3.53 (1H, s), 3.55 (1H, s), 3.74 (2H, m), 4.00–4.20 (4H, m), 4.29 (1H, br-s), 7.15–7.30 (4H, m) MS (TSP); m/z 349 (MH⁺)

(e) 1'-(tert-Butoxycarbonyl)-2,3-dihydro-5-methylspiro[isoquinoline-4(1H),4'-piperidin]-1-one 1-(Ethoxycarbonyl)-4-(ethoxycarbonylaminomethyl)-4-(2-methylphenyl)-piperidine (327 mg) was dissolved in polyphosphoric acid (6.5 g) and stirred at 150° C. for 2 hours. The reaction mixture was added with ice (30 g), adjusted to pH 12 with 5 N aqueous sodium hydroxide and then extracted twice with dichloromethane (30 ml). The organic layer was dried over anhydrous magnesium sulfate, and then the solvent was evaporated under reduced pressure. The residue was dissolved in dichloromethane (10 ml). The reaction mixture was added with di-tert-butyl dicarbonate (0.43 ml) and triethylamine (0.26 ml) and stirred at room temperature for 1 hour. The reaction mixture was added with water (10 ml), and the layers were separated. Then, the aqueous layer was further extracted with dichloromethane (10 ml). The organic layer was dried over anhydrous magnesium sulfate, and then the solvent was evaporated under reduced pressure. The residue was purified by silica gel column chromatography (elution solvent: hexane:ethyl acetate=1:2 ethyl acetate) to obtain 102 mg of the title compound. Yield: 33% (for two steps).

¹H-NMR (CDCl₃); δ (ppm) 1.49 (9H, m), 1.73 (2H, d, J=12Hz), 2.41 (2H, m), 2.56 (3H, s), 2.99 (2H, t, J=12Hz), 3.59 (2H, s), 4.04 (2H, m), 6.17 (1H, br-s), 7.25–7.35 (2H, m), 8.04 (1H, d, J=8Hz) MS (TSP); m/z 331 (MH⁺)

(f) 2,3-Dihydro-5-methylspiro[isoquinoline-4(1H),4'-piperidin]-1-one Trifluoroacetate The title compound was obtained in the same manner in Reference Example 2, (d) from 1'-(tert-butoxycarbonyl)-2,3-dihydro-5-methylspiro[isoquinoline-4(1H),4'-piperidin]-1-one. Yield: 100%.

¹H-NMR (D₂O); δ (ppm) 1.96 (2H, d, J=14Hz), 2.60 (3H, s), 2.70 (2H, td, J=14Hz,4Hz), 3.26 (2H, t, J=14Hz), 3.43 (2H, dd, J=14Hz, 4Hz), 3.63 (2H, s), 7.36 (1H, t, J=8Hz), 7.46 (1H, d, J=8Hz), 7.84 (1H, d, J=8Hz) MS (EI); m/z 230 (M⁺)

Reference Example 4

4-Bromo-1-(4-diethylcarbamoylphenyl)-1-(3-methoxyphenyl)-1-butene (a) 1-Cyclopropyl-1-(4-diethylcarbamoylphenyl)-1-(3-methoxyphenyl)Methanol A solution of cyclopropyl bromide (0.31 ml) dissolved in tetrahydrofuran (1.5 ml) was added with magnesium (46.9 mg) and stirred at 60° C. for 1 hour to prepare a Grignard reagent. The Grignard reagent was added with a solution of 3-(4-diethylcarbamoylbenzoyl)anisole (150 mg) synthesized in accordance with the method described in WO97/10230, which was dissolved in tetrahydrofuran (1.5 ml), and then stirred at 60° C. for 2 hours. The reaction mixture was added with saturated aqueous ammonium chloride (4 ml) with ice cooling to terminate the reaction and then extracted twice with dichloromethane (4 ml). The organic layer was dried over anhydrous magnesium sulfate, and then the solvent was evaporated under reduced pressure. The residue was purified by silica gel column chromatography (elution solvent: hexane:ethyl acetate=2:1→1:1) to obtain 90.9 mg of the title compound. Yield: 53%.

¹H-NMR (CDCl₃); δ (ppm) 0.45–0.65 (4H, m), 1.12 (3H, br-s), 1.22 (3H, br-s), 1.60 (1H, m), 2.10 (1H, s), 3.27 (2H, br-s), 3.54 (2H, br-s), 3.78 (3H, s), 6.80 (1H, dd, J=8Hz, 3Hz), 6.99 (1H, d, J=8Hz), 7.06 (1H, m), 7.20–7.35 (3H, m), 7.45 (2H, d, J=8Hz) MS (TSP); m/z 354 (MH⁺)

(b) 4-Bromo-1-(4-diethylcarbamoylphenyl)-1-(3-methoxyphenyl)-1-butene

1-Cyclopropyl-1-(4-diethylcarbamoylphenyl)-1-(3-methoxyphenyl)Methanol (90.9 mg) was dissolved in acetic acid (1.8 ml), added with 48% hydrobromic acid (1.8 ml) with ice cooling and stirred at room temperature for 1.5 hours. The reaction mixture was added with water (5 ml) and extracted twice with dichloromethane (5 ml). The organic layer was dried over anhydrous magnesium sulfate, and then the solvent was evaporated under reduced pressure to obtain 102 mg of the title compound. Yield: 95%.

¹H-NMR (CDCl₃); δ (ppm) 1.10–1.30 (6H, m), 2.69 (2H, m), 3.32 (2H, br-s), 3.43 (2H, m), 3.56 (2H, br-s), 3.77 (1.5H, s), 3.80 (1.5H, s), 6.10 (0.5H, t, J=7Hz), 6.12 (0.5H, t, J=7Hz), 6.70–6.90 (3H, m), 7.15–7.45 (5H, m) MS (FAB); m/z 416 (M⁺), 418

Example 1

1-[3-(4-Diethylcarbamoylphenyl)-3-(3-methoxyphenyl)propyl]-4-(1,3-dihydro-2H-benzimidazol-2-on-1-yl)Piperidine 4-(1,3-Dihydro-2H-benzimidazol-2-on-1-yl)piperidine (47.9 mg) was dissolved in N,N-dimethylformamide (1 ml), added with the 1-bromo-3-(4-diethylcarbamoyl-phenyl)-3-(3-methoxyphenyl)propane (107 mg) obtained in Reference Example 1 and potassium carbonate (36.5 mg) and stirred at room temperature for 17 hours. The reaction mixture was added with water (4 ml) and extracted twice with dichloromethane (4 ml). The organic layer was dried over anhydrous magnesium sulfate, and then the solvent was evaporated under reduced pressure. The residue was purified by preparative thin layer silica gel column chromatography (developing solvent: ethyl acetate:methanol=10:1) to obtain 100 mg of the title compound. Yield: 84%.

¹H-NMR (CDCl₃); δ (ppm) 1.11 (3H, br-s), 1.22 (3H, br-s), 1.81 (2H, d, J=12Hz), 2.10–2.60 (8H, m), 3.12 (2H, m), 3.26 (2H, br-s), 3.54 (2H, br-s), 3.78 (3H, s), 4.00 (1H, t, J=7Hz), 4.38 (1H, m), 6.70–6.90 (3H, m), 7.00–7.15 (3H, m), 7.20–7.40 (6H, m), 9.75 (1H, s) MS (TSP); m/z 541 (MH⁺)

Example 2

1-[3-(4-Diethylcarbamoylphenyl)-3-(3-hydroxyphenyl)Propyl]-4-(1,3-dihydro-2H-benzimidazol-2-on-1-yl)Piperidine Hydrochloride The 1-[3-(4-diethylcarbamoylphenyl)-3-(3-methoxyphenyl)propyl]-4-(1,3-dihydro-2H-benzimidazol-2-on-1-yl)piperidine (1.196 g) obtained in Example 1 was dissolved in dichloromethane (24 ml), added with a solution of boron tribromide in dichloromethane (1.0 M, 8.8 ml) and stirred at room temperature for 2 hours. The reaction mixture was slowly added with methanol (6 ml) with ice cooling to quench the reaction and then added with 7.5 N aqueous ammonia (40 ml). The layers were separated, and the aqueous layer was extracted with dichloromethane (20 ml). The organic layer was dried over anhydrous magnesium sulfate, and then the solvent was evaporated under reduced pressure. The residue was dissolved in methanol (24 ml) and added with a solution of hydrochloric acid in methanol (8.8 ml), and then the solvent was evaporated under reduced pressure again. The residue was purified by LH-20 column chromatography (elution solvent: dichloromethane:methanol=1:1) to obtain 1.057 g of the title compound. Yield: 85%.

1H-NMR (DMSO-d$_6$); δ (ppm) 1.08 (6H, m), 1.85 (2H, m), 2.78 (2H, m), 2.94 (4H, m), 3.15 (4H, m), 3.48 (2H, br-s), 3.64 (2H, br-s), 3.99 (1H, m), 4.51 (1H, m), 6.61 (1H, d, J=8Hz), 6.72 (1H, s), 6.81 (1H, d, J=8Hz), 6.99 (3H, m), 7.11 (1H, t, J=8Hz), 7.29 (2H, d, J=8Hz), 7.38 (2H, d, J=8Hz), 7.52 (1H, m), 9.98 (1H, s) MS (FAB); m/z 527 (MH$^+$)

Example 3

8-[3-(4-Diethylcarbamoylphenyl)-3-(3-methoxyphenyl)Propyl]-1-phenyl-1,3,8-triazaspiro[4,5]decan-4-one The title compound was obtained in the same manner in Example 1 from the 1-bromo-3-(4-diethylcarbamoylphenyl)-3-(3-methoxyphenyl)propane obtained in Reference Example 1 and 1-phenyl-1,3,8-triazaspiro[4,5]decan-4-one. Yield: 61%.

$^1$H-NMR (CDCl$_3$); δ (ppm) 1.11 (3H, br-s), 1.21 (3H, br-s), 1.79 (2H, d, J=12Hz), 2.20–2.50 (4H, m), 2.60–3.00 (6H, m), 3.26 (2H, br-s), 3.52 (2H, br-s), 3.79 (3H, s), 3.99 (1H, m), 4.89 (2H, s), 6.70–7.00 (7H, m), 7.15–7.35 (7H, m) MS (TSP); m/z 555 (MH$^+$)

Example 4

1-[3-(4-Diethylcarbamoylphenyl)-3-(3-methoxyphenyl)Propyl]-4-(2-hydroxymethyl-1H-benzimidazol-1-yl)Piperidine The title compound was obtained in the same manner in Example 1 from the 1-bromo-3-(4-diethylcarbamoylphenyl)-3-(3-methoxyphenyl)propane obtained in Reference Example 1 and 4-(2-hydroxymethyl-1H-benzimidazol-1-yl)piperidine trifluoroacetate obtained in the same manner in Reference Example 2. Yield: 59%.

$^1$H-NMR (CDCl$_3$); δ (ppm) 1.12 (3H, br-s), 1.23 (3H, br-s), 1.90 (2H, m), 2.16 (2H, m), 2.28 (2H, m), 2.39 (2H, m), 2.53(2H, m), 3.08 (2H, m), 3.25 (2H, br-s), 3.55 (2H, br-s), 3.80 (3H, s), 4.01 (1H, m), 4.39 (1H, m), 4.88 (2H, s), 6.75 (1H, d, J=8Hz), 6.82 (1H, s), 6.89 (1H, d, J=8Hz), 7.26 (7H, m), 7.69 (2H, m) MS (FAB); m/z 555 (MH$^+$)

Example 5

1'-[3-(4-Diethylcarbamoylphenyl)-3-(3-methoxyphenyl)Propyl]-2,3-dihydro-5-methylspiro[isoquinoline-4(1H),4'-piperidin]-1-one The title compound was obtained in the same manner in Example 1 from the 1-bromo-3-(4-diethylcarbamoylphenyl)-3-(3-methoxyphenyl)propane obtained in Reference Example 1 and the 2,3-dihydro-5-methylspiro[isoquinoline-4(1H),4'-piperidin]-1-one trifluoroacetate obtained in Reference Example 3. Yield: 70%.

$^1$H-NMR (CDCl$_3$); δ (ppm) 1.10 (3H, br-s), 1.22 (3H, br-s), 1.73 (2H, m), 2.14 (2H, m), 2.25 (2H, m), 2.31 (2H, m), 2.58 (2H, m), 2.67 (3H, s), 2.81 (2H, m), 3.26 (2H, br-s), 3.53 (4H, m), 3.79 (3H, s), 4.00 (1H, t, J=8Hz), 6.75 (1H, d, J=8Hz), 6.81 (1H, s), 6.86 (1H, d, J=8Hz), 7.20–7.29 (8H, m), 8.03 (1H, d, J=8Hz) MS (FAB); m/z 554 (MH$^+$)

Example 6

1'-[3-(4-Diethylcarbamoylphenyl)-3-(3-hydroxyphenyl)Propyl]-2,3-dihydro-5-methylspiro[isoquinoline-4(1H),4'-piperidin]-1-one Hydrochloride The title compound was obtained in the same manner in Example 2 from the 1'-[3-(4-diethylcarbamoylphenyl)-3-(3-methoxyphenyl)propyl]-2,3-dihydro-5-methylspiro[isoquinoline-4(1H),4'-piperidin]-1-one obtained in Example 5. Yield: 43%.

1H-NMR (CDCl$_3$); δ (ppm) 1.09 (3H, br-s), 1.24 (3H, br-s), 1.67 (2H, m), 2.21 (4H, m), 2.36 (2H, m), 2.57 (3H, s), 2.72 (2H, m), 2.88 (2H, m), 3.22 (2H, br-s), 3.45 (4H, m), 3.83 (1H, m), 6.67 (4H, m), 7.12 (7H, m), 8.00 (1H, m) MS (TSP); m/z 540 (MH$^+$)

Example 7

1-[3-(4-Diethylcarbamoylphenyl)-3-(2-methoxyphenyl)Propyl]-4-(1,3-dihydro-2H-benzimidazol-2-on-1-yl)Piperidine The title compound was obtained in the same manner in Example 1 from 1-bromo-3-(4-diethylcarbamoylphenyl)-3-(2-methoxyphenyl)propane obtained in the same manner in Reference Example 1 and 4-(1,3-dihydro-2H-benzimidazol-2-on-1-yl)piperidine. Yield: 49%.

$^1$H-NMR (CDCl$_3$); δ (ppm) 1.11 (3H, br-s), 1.22 (3H, br-s), 1.81 (2H, m), 2.12 (2H, m), 2.26 (2H, m), 2.37 (2H, m), 2.46 (2H, m), 3.08 (2H, m), 3.27 (2H, br-s), 3.53 (2H, br-s), 3.78 (3H, s), 4.36 (1H, m), 4.46 (1H, m), 6.85 (1H, m), 6.93 (1H, m), 7.06 (3H, m), 7.19 (1H, m), 7.29 (6H, m), 9.61 (1H, s) MS (TSP); m/z 541 (MH$^+$)

Example 8

8-[3-(4-Diethylcarbamoylphenyl)-3-(2-methoxyphenyl)Propyl]-1-phenyl-1,3,8-triazaspiro[4,5]decan-4-one The title compound was obtained in the same manner in Example 1 from 1-bromo-3-(4-diethylcarbamoylphenyl)-3-(2-methoxyphenyl)propane obtained in the same manner in Reference Example 1 and 1-phenyl-1,3,8-triazaspiro[4,5]decan-4-one. Yield: 75%.

$^1$H-NMR (CDCl$_3$); δ (ppm) 1.11 (3H, br-s), 1.22 (3H, br-s), 1.72 (2H, m), 2.24 (2H, m), 2.39 (2H, m), 2.67 (2H, m), 2.79 (4H, m), 3.26 (2H, br-s), 3.52 (2H, br-s), 3.76 (3H, s), 4.50 (1H, m), 4.71 (2H, s), 6.84 (2H, m), 6.93 (4H, m), 7.18 (1H, m), 7.29 (7H, m) MS (TSP); m/z 555 (MH$^+$)

Example 9

1'-[3-(4-Diethylcarbamoylphenyl)-3-(2-methoxyphenyl)Propyl]-2,3-dihydro-5-methylspiro[isoquinoline-4(1H),4'-piperidin]-1-one The title compound was obtained in the same manner in Example 1 from 1-bromo-3-(4-diethylcarbamoylphenyl)-3-(2-methoxyphenyl)propane obtained in the same manner in Reference Example 1 and the 2,3-dihydro-5-methylspiro-[isoquinoline-4(1H),4'-piperidin]-1-one trifluoroacetate obtained in Reference Example 3. Yield: 63%.

$^1$H-NMR (CDCl$_3$); δ (ppm) 1.11 (3H, br-s), 1.22 (3H, br-s), 1.72 (2H, m), 2.21 (4H, m), 2.34 (2H, m), 2.59 (2H, m), 2.66 (3H, s), 2.83 (2H, m), 3.26 (2H, br-s), 3.52 (4H, m), 3.77 (3H, s), 4.47 (1H, m), 6.84 (1H, m), 6.93 (1H, m), 7.27 (9H, m), 8.02 (1H, m) MS (TSP); m/z 554 (MH$^+$)

Example 10

1-[3-(4-Diethylcarbamoylphenyl)-3-(2-methoxyphenyl)Propyl]-4-(2-hydroxymethyl-1H-benzimidazol-1-yl) Piperidine The title compound was obtained in the same manner in Example 1 from 1-bromo-3-(4-diethylcarbamoylphenyl)-3-

(2-methoxyphenyl)propane obtained in the same manner in Reference Example 1 and 4-(2-hydroxymethyl-1H-benzimidazol-1-yl)piperidine trifluoroacetate obtained in the same manner in Reference Example 2. Yield: 29%.

$^1$H-NMR (CDCl3); δ (ppm) 1.11 (3H, br-s), 1.21 (3H, br-s), 1.89 (2H, m), 2.17 (2H, m), 2.25 (2H, m), 2.40 (2H, m), 2.58 (2H, m), 3.08 (2H, m), 3.27 (2H, br-s), 3.53 (2H, br-s), 3.80 (3H, s), 4.39 (1H, m), 4.48 (1H, t, J=7Hz), 4.87 (2H, s), 6.77 (1H, d, J=8Hz), 6.79 (1H, t, J=8Hz), 7.25 (8H, m), 7.69 (2H, m) MS (TSP); m/z 555 (MH$^+$)

Example 11

1-[3-(4-Diethylcarbamoylphenyl)-3-(3-methoxyphenyl)Propyl]-4-(1H-benzimidazol-1-yl)Piperidine The title compound was obtained in the same manner in Example 1 from the 1-bromo-3-(4-diethylcarbamoylphenyl)-3-(3-methoxyphenyl)propane obtained in Reference Example 1 and the 4-(1H-benzimidazol-1-yl)piperidine trifluoroacetate obtained in Reference Example 2. Yield: 65%.

$^1$H-NMR (CDCl$_3$); δ (ppm) 1.10 (3H, br-s), 1.22 (3H, br-s), 2.16 (6H, m), 2.27 (2H, m), 2.36 (2H, m), 3.08 (2H, m), 3.26 (2H, br-s), 3.53 (2H, br-s), 3.79 (3H, s), 4.02 (1H, t, J=7Hz), 4.19 (1H, m), 6.75 (1H, d, J=8Hz), 6.83 (1H, s), 6.87 (1H, d, J=8Hz), 7.23 (1H, t, J=8Hz), 7.28 (6H, m), 7.43 (1H, m), 7.81 (1H, m), 7.98 (1H, s) MS (TSP); m/z 525 (MH$^+$)

Example 12

1-[3-(4-Diethylcarbamoylphenyl)-3-(4-methoxyphenyl)Propyl]-4-(1,3-dihydro-2H-benzimidazol-2-on-1-yl)Piperidine The title compound was obtained in the same manner in Example 1 from 1-bromo-3-(4-diethylcarbamoylphenyl)-3-(4-methoxyphenyl)propane obtained in the same manner in Reference Example 1 and 4-(1,3-dihydro-2H-benzimidazol-2-on-1-yl)piperidine. Yield: 65%.

1H-NMR (CDCl$_3$); δ (ppm) 1.11 (3H, br-s), 1.22 (3H, br-s), 1.80 (2H, m), 2.11 (2H, m), 2.25 (2H, m), 2.32 (2H, m), 2.46 (2H, m), 3.04 (2H, m), 3.26 (2H, br-s), 3.53 (2H, br-s), 3.78 (3H, s), 3.99 (1H, m), 4.34 (1H, m), 6.84 (2H, d, J=8Hz), 7.06 (2H, m), 7.18 (2H, d, J=8Hz), 7.28 (6H, m), 9.58 (1H, s) MS (FAB); m/z 541 (MH$^+$)

Example 13

1-[3-(4-Diethylcarbamoylphenyl)-3-(4-hydroxyphenyl)Propyl]-4-(1,3-dihydro-2H-benzimidazol-2-on-1-yl)Piperidine Hydrochloride The title compound was obtained in the same manner in Example 2 from the 1-[3-(4-diethylcarbamoylphenyl)-3-(4-methoxyphenyl)propyl]-4-(1,3-dihydro-2H-benzimidazol-2-on-1-yl)piperidine obtained in Example 12. Yield: 13%.

$^1$H-NMR (CDCl$^3$); δ (ppm) 1.10 (3H, br-s), 1.22 (3H, br-s), 1.79 (2H, m), 2.29 (4H, m), 2.48 (4H, m), 3.11 (2H, m), 3.23 (2H, br-s), 3.52 (2H, br-s), 3.86 (1H, m), 4.41 (1H, m), 6.59 (2H, m), 7.00 (6H, m), 7.26 (3H, m), 7.38 (1H, m), 9.86 (1H, s) MS (TSP); m/z 527 (MH$^+$)

Example 14

1-[3-(4-Diethylcarbamoylphenyl)-3-(3-methoxyphenyl)Propyl]-4-(2-methyl-1H-benzimidazol-1-yl)Piperidine The title compound was obtained in the same manner in Example 1 from the 1-bromo-3-(4-diethylcarbamoylphenyl)-3-(3-methoxyphenyl)propane obtained in Reference Example 1 and 4-(2-methyl-1H-benzimidazol-1-yl)piperidine trifluoroacetate obtained in the same manner in Reference Example 2. Yield: 61%.

$^1$H-NMR (CDCl$_3$); δ (ppm) 1.11 (3H, br-s), 1.23 (3H, br-s), 1.84 (2H, m), 2.11 (2H, m), 2.28 (2H, m), 2.38 (2H, m), 2.56 (2H, m), 2.62 (3H, s), 3.10 (2H, m), 3.27 (2H, br-s), 3.52 (2H, br-s), 3.80 (3H, s), 4.01 (1H, t, J=7Hz), 4.13 (1H, m), 6.76 (1H, d, J=8Hz), 6.83 (1H, s), 6.89 (1H, d, J=8Hz), 7.19–7.31 (7H, m), 7.58 (1H, m), 7.68 (1H, m) MS (EI); m/z 538 (M$^+$)

Example 15

1-[3-(4-Diethylcarbamoylphenyl)-3-(2-hydroxyphenyl)Propyl]-4-(1,3-dihydro-2H-benzimidazol-2-on-1-yl)Piperidine Hydrochloride The title compound was obtained in the same manner in Example 2 from the 1-[3-(4-diethylcarbamoylphenyl)-3-(2-methoxyphenyl)propyl]-4-(1,3-dihydro-2H-benzimidazol-2-on-1-yl)piperidine obtained in Example 7. Yield: 31%.

$^1$H-NMR (DMSO-d$_6$); δ (ppm) 1.22 (6H, br-s), 1.89 (2H, m), 2.65 (2H, m), 2.98 (2H, m), 3.16 (4H, m), 3.39 (2H, br-s), 3.58 (4H, m), 4.38 (1H, t, J=7Hz), 4.47 (1H, m), 6.81 (2H, m), 7.03 (4H, m), 7.28 (4H, m), 7.37 (2H, d, J=8Hz), 9.98 (1H, s) MS (TSP); m/z 527 (MH$^+$)

Example 16

1-[3-(3-Diethylcarbamoylphenyl)-3-(3-methoxyphenyl)Propyl]-4-(1,3-dihydro-2H-benzimidazol-2-on-1-yl)Piperidine The title compound was obtained in the same manner in Example 1 from 1-bromo-3-(3-diethylcarbamoylphenyl)-3-(3-methoxyphenyl)propane obtained in the same manner in Reference Example 1 and 4-(1,3-dihydro-2H-benzimidazol-2-on-1-yl)piperidine. Yield: 81%.

$^1$H-NMR (CDCl$_3$); δ (ppm) 1.03 (3H, br-s), 1.24 (3H, br-s), 1.80 (2H, d, J=12Hz), 2.12 (2H, t, J=12Hz), 2.20–2.60 (6H, m), 3.05 (2H, d, J=12Hz), 3.18 (2H, br-s), 3.52 (2H, br-s), 3.78 (3H, s), 4.01 (1H, t, J=7Hz), 4.34 (1H, m), 6.70–6.90 (3H, m), 7.00–7.10 (2H, m), 7.15–7.35 (7H, m), 9.43 (1H, s) MS (TSP); m/z 541 (MH$^+$)

Example 17

1-[3-(4-Diethylcarbamoylphenyl)-3-(3-methoxyphenyl)Propyl]-4-(3-benzyl-1,3-dihydro-2H-benzimidazol-2-on-1-yl)Piperidine The 1-[3-(4-diethylcarbamoylphenyl)-3-(3-methoxyphenyl)propyl]-4-(1,3-dihydro-2H-benzimidazol-2-on-1-yl)piperidine (50 mg) obtained in Example 1 was dissolved in N,N-dimethylformamide (1 ml), added with sodium hydride (60% in oil, 7.4 mg) and stirred at room temperature for 1.5 hours. The reaction mixture was added with benzyl bromide (22 μl) and further stirred at 60° C. for 2 hours. The reaction mixture was added with water (5 ml) and extracted twice with ethyl acetate (5 ml). The organic layer was washed with water (10 ml) and dried over anhydrous magnesium sulfate, and then the solvent was evaporated under reduced pressure. The residue was purified by preparative thin layer silica gel column chromatography (developing solvent: ethyl acetate:methanol=10:1) to obtain 33 mg of the title compound. Yield: 57%.

$^1$H-NMR (CDCl$_3$); δ (ppm) 1.12 (3H, br-s), 1.22 (3H, br-s), 1.82 (2H, m), 2.11 (2H, m), 2.27 (2H, m), 2.33 (2H, m), 2.47 (2H, m), 3.04 (2H, m), 3.26 (2H, br-s), 3.53 (2H, br-s), 3.79 (3H, s), 4.02 (1H, m), 4.40 (1H, m), 5.06 (2H, s), 6.74 (1H, d, J=8Hz), 6.82 (1H, s), 6.88 (2H, m), 6.99 (2H, m), 7.25 (11H, m) MS (TSP); m/z 631 (MH$^+$)

Example 18

1-[3-(4-Diethylcarbamoylphenyl)-3-(3-methoxyphenyl)Propyl]-4-(3-cyclopropylmethyl-1,3-dihydro-2H-benzimidazol-2-on-1-yl)Piperidine The title compound was obtained in the same manner in Example 17 from the 1-[3-(4-diethylcarbamoylphenyl)-3-(3-methoxyphenyl)propyl]-4-(1,3-dihydro-2H-benzimidazol-2-on-1-yl)piperidine obtained in Example 1. Yield: 59%.

$^1$H-NMR (CDCl$_3$); δ (ppm) 0.43 (2H, m), 0.54 (2H, m), 1.11 (3H, br-s), 1.22 (3H, br-s), 1.26 (1H, m), 1.81 (2H, m), 2.10 (2H, m), 2.27 (2H, m), 2.33 (2H, m), 2.45 (2H, m), 3.03 (2H, m), 3.26 (2H, br-s), 3.53 (2H, br-s), 3.78 (5H, m), 4.02 (1H, m), 4.36 (1H, m), 6.74 (1H, d, J=8Hz), 6.82 (1H, s), 6.87 (1H, d, J=8Hz), 7.07 (2H, m), 7.22 (1H, t, J=8Hz), 7.30 (6H, m) MS (TSP); m/z 595 (MH$^+$)

Example 19

1-[4-(4-Diethylcarbamoylphenyl)-4-(3-methoxyphenyl)Butyl]-4-(1,3-dihydro-2H-benzimidazol-2-on-1-yl)Piperidine 1-[4-(4-Diethylcarbamoylphenyl)-4-(3-methoxyphenyl)-4-butenyl]-4-(1,3-dihydro-2H-benzimidazol-2-on-1-yl)piperidine was obtained in the same manner in Example 1 from the 4-bromo-1-(4-diethylcarbamoylphenyl)-1-(3-methoxyphenyl)-1-butene obtained in Reference Example 4 and 4-(1,3-dihydro-2H-benzimidazol-2-on-1-yl)piperidine. Yield: 58%.

The title compound was obtained in the same manner in Reference Example 1, (a) from the obtained 1-[4-(4-diethylcarbamoylphenyl)-4-(3-methoxyphenyl)-4-butenyl]-4-(1,3-dihydro-2H-benzimidazol-2 -on-1-yl)piperidine. Yield: 44%.

$^1$H-NMR (CDCl$_3$); δ (ppm) 1.10 (3H, br-s), 1.22 (3H, br-s), 1.80 (2H, d, J=12Hz), 2.00–2.20 (6H, m), 2.40–2.60 (4H, m), 3.06 (2H, m), 3.25 (2H, br-s), 3.52 (2H, br-s), 3.78 (3H, s), 3.90 (1H, t, J=7Hz), 4.38 (1H, m), 6.74 (1H, dd, J=8Hz,3Hz), 6.80 (1H, s), 6.85 (1H, d, J=8Hz), 7.00–7.10 (3H, m), 7.15–7.35 (6H, m), 9.55 (1H, s) MS (TSP); m/z 555 (MH$^+$)

Example 20

1-[3-(4-Diethylcarbamoylphenyl)-3-(3-methoxyphenyl)Propyl]-4-(3,3-dimethyl-2,3-dihydro-1H-indol-2-on-1-yl)Piperidine The title compound was obtained in the same manner in Example 1 from the 1 -bromo-3-(4-diethylcarbamoylphenyl)-3-(3-methoxyphenyl)propane obtained in Reference Example 1 and 4-(3,3-dimethyl-2,3-dihydro-1H-indol-2-on-1-yl)piperidine trifluoroacetate obtained in the same manner in Reference Example 2. Yield: 67%.

$^1$H-NMR (CDCl$_3$); δ (ppm) 1.11 (3H, br-s), 1.23 (3H, br-s), 1.35 (6H, s), 1.67 (2H, m), 2.08 (2H, m), 2.26 (2H, m), 2.32 (2H, m), 2.46 (2H, m), 3.04 (2H, m), 3.26 (2H, br-s), 3.52 (2H, br-s), 3.79 (3H, s), 4.01 (1H, m), 4.28 (1H, m), 6.74 (1H, m), 6.81 (1H, s), 6.86 (1H, m), 7.04 (1H, m), 7.20–7.29 (8H, m) MS (TSP); m/z 568 (MH$^+$)

Example 21

1-[3-(4-Diethylcarbamoylphenyl)-3-(3-fluorophenyl)Propyl]-4-(1,3-dihydro-2H-benzimidazol-2-on-1-yl)Piperidine The title compound was obtained in the same manner in Example 1 from 1-bromo-3-(4-diethylcarbamoylphenyl)-3-(3-fluorophenyl)propane obtained in the same manner in Reference Example 1 and 4-(1,3-dihydro-2H-benzimidazol-2-on-1-yl)piperidine. Yield: 67%.

$^1$H-NMR (CDCl$_3$); δ (ppm) 1.12 (3H, br-s), 1.22 (3H, br-s), 1.80 (2H, d, J=12Hz), 2.11 (2H, t, J=12Hz), 2.20–2.40 (4H, m), 2.47 (2H, q, J=12Hz), 3.03 (2H, d, J=12Hz), 3.26 (2H, br-s), 3.53 (2H, br-s), 4.06 (1H, t, J=7Hz), 4.33 (1H, m), 6.90 (1H, t, J=8Hz), 6.96 (1H, d, J=8Hz), 7.00–7.10 (4H, m), 7.20–7.35 (6H, m), 8.83 (1H, s) MS (TSP); m/z 529 (MH$^+$)

Example 22

8-[3-(4-Diethylcarbamoylphenyl)-3-(3-hydroxyphenyl)Propyl]-1-phenyl-1,3,8-triazaspiro[4,5]decan-4-One Hydrochloride The title compound was obtained in the same manner in Example 2 from the 8-[3-(4-diethylcarbamoylphenyl)-3-(3-methoxyphenyl)propyl]-1-phenyl-1,3,8-triazaspiro[4,5]decan-4-one obtained in Example 3. Yield: 92%.

$^1$H-NMR (CD$_3$OD); δ (ppm) 1.03 (3H, br-s), 1.16 (3H, br-s), 1.92 (2H, m), 2.53 (2H, m), 2.76 (2H, m), 3.00 (2H, m), 3.25 (2H, br-s), 3.48 (4H, m), 3.67 (2H, m), 3.95 (1H, t, J=7Hz), 4.64 (2H, s), 6.55 (1H, m), 6.66 (1H, s), 6.74 (1H, d, J=8Hz), 6.82 (1H, t, J=8Hz), 6.95 (2H, d, J=8Hz), 7.05 (1H, t, J=8Hz), 7.21 (2H, t, J=8Hz), 7.26 (2H, d, J=8Hz), 7.37 (2H, d, J=8Hz) MS (TSP); m/z 541 (MH$^+$)

Example 23

1-[3-(4-Diethylcarbamoylphenyl)-3-(1,3-benzodioxol-5-yl)Propyl]-4-(1,3-dihydro-2H-benzimidazol-2-on-1-yl)Piperidine The title compound was obtained in the same manner in Example 1 from 1-bromo-3-(4-diethylcarbamoylphenyl)-3-(1,3-benzodioxol-5-yl)propane obtained in the same manner in Reference Example 1 and 4-(1,3-dihydro-2H-benzimidazol-2-on-1-yl)piperidine. Yield: 58%.

$^1$H-NMR (CDCl$_3$); δ (ppm) 1.12 (3H, br-s), 1.23 (3H, br-s), 1.80 (2H, m), 2.13 (2H, m), 2.23 (2H, m), 2.34 (2H, m), 2.46 (2H, m), 3.05 (2H, m), 3.27 (2H, br-s), 3.53 (2H, br-s), 3.96 (1H, t, J=7Hz), 4.34 (1H, m), 5.92 (2H, s), 6.73 (3H, m), 7.06 (3H, m), 7.30 (5H, m), 9.78 (1H, s) MS (TSP); m/z 555 (MH$^+$)

Example 24

1-[4-(4-Diethylcarbamoylphenyl)-4-(3-hydroxyphenyl)Butyl]-4-(1,3-dihydro-2H-benzimidazol-2-on-1-yl)Piperidine Hydrochloride 1-[4-(4-Diethylcarbamoylphenyl)-4-(3-hydroxyphenyl)-4-butenyl]-4-(1,3-dihydro-2H-benzimidazol-2-on-1-yl) piperidine hydrochloride was obtained in the same manner in Example 2 from the 1-[4-(4-diethylcarbamoylphenyl)-4-(3-methoxyphenyl)-4-butenyl]-4-(1,3-dihydro-2H-benzimidazol-2-on-1-yl)piperidine obtained in the course of Example 19. Yield: 77%.

The title compound was obtained in the same manner in Reference Example 1, (a) from the obtained 1-[4-(4- diethylcarbamoylphenyl)-4-(3-hydroxyphenyl)-4-butenyl]-4-(1,3-dihydro-2H-benzimidazol-2-on-1-yl)piperidine hydrochloride. Yield: 74%.

$^1$H-NMR (CD$_3$OD); δ (ppm) 1.10 (3H, br-s), 1.22 (3H, br-s), 1.74 (2H, m), 1.98 (2H, d, J=12Hz), 2.14 (2H, m), 2.77 (2H, q, J=12Hz), 3.00–3.20 (4H, m), 3.30 (2H, br-s), 3.45–3.65 (4H, m), 3.97 (1H, t, J=7Hz), 4.53 (1H, m), 6.62 (1H, d, J=8Hz), 6.74 (1H, s), 6.79 (1H, d, J=8Hz), 7.00–7.15 (4H, m), 7.25–7.35 (5H, m) MS (TSP); m/z 541 (MH$^+$)

Example 25

1-[3-(4-Diethylcarbamoylphenyl)-3-(3,4-dihydroxyphenyl)Propyl]-4-(1,3-dihydro-2H-benzimidazol-2-on-1-yl)Piperidine Hydrochloride The title compound was obtained in similar manner to that of Example 2 from the 1-[3-(4-diethylcarbamoylphenyl)-3-(1,3-benzodioxol-5-yl)propyl]-4-(1,3-dihydro-2H-benzimidazol-2-on-1-yl)piperidine obtained in Example 23. Yield: 10%.

$^1$H-NMR (CD$_3$OD); δ (ppm) 1.10 (3H, br-s), 1.22 (3H, br-s), 1.75 (2H, m), 2.23 (4H, m), 2.45 (4H, m), 3.14 (2H, m), 3.30 (2H, br-s), 3.51 (2H, br-s), 3.87 (1H, m), 4.30 (1H, m), 6.65 (3H, m), 7.04 (3H, m), 7.32 (5H, m) MS (FAB); m/z 543 (MH$^+$)

Example 26

1-[3-(4-Diethylcarbamoylphenyl)-3-(3-methoxyphenyl)Propyl]-4-(1H-indol-3-yl)Piperidine The title compound was obtained in the same manner in Example 1 from the 1-bromo-3-(4-diethylcarbamoylphenyl)-3-(3-methoxyphenyl)propane obtained in Reference Example 1 and 4-(1H-indol-3-yl)piperidine hydrochloride synthesized in accordance with the descriptions of J. Org. Chem., 1975, 40, 2525 and Helv. Chim. Acta, 1968, 51, 260. Yield: 79%.

$^1$H-NMR (CDCl$_3$); δ (ppm) 1.11 (3H, br-s), 1.23 (3H, br-s), 1.85 (2H, m), 2.07 (4H, m), 2.34 (4H, m), 2.83 (1H, m), 3.03 (2H, m), 3.26 (2H, br-s), 3.53 (2H, br-s), 3.78 (3H, s), 3.98 (1H, t, J=7Hz), 6.74 (1H, d, J=8Hz), 6.82 (1H, s), 6.86 (1H, d, J=8Hz), 6.98 (1H, s), 7.09 (1H, t, J=8Hz), 7.20 (2H, m), 7.29 (4H, m), 7.35 (1H, d, J=8Hz), 7.63 (1H, d, J=8Hz), 8.02 (1H, s MS (TSP); m/z 524 (MH$^+$)

Example 27

1-[3-(4-Diethylcarbamoylphenyl)-3-(3-hydroxyphenyl)Propyl]-4-(1H-indol-3-yl)Piperidine Hydrochloride The title compound was obtained in the same manner in Example 2 from the 1[3-(4-diethylcarbamoylphenyl)-3-(3-methoxyphenyl)propyl]-4-(H-indol-3-yl)-piperidine obtained in Example 26. Yield: 69%.

$^1$H-NMR (CDCl$_3$, free base); δ (ppm) 1.07 (3H, br-s), 1.23 (3H, br-s), 1.83 (2H, m), 1.98 (2H, m), 2.14 (2H, m), 2.28 (2H, m), 2.38 (2H, m), 2.80 (1H, m), 2.95 (1H, m), 3.09 (1H, m), 3.22 (2H, br-s), 3.53 (2H, br-s), 3.84 (1H, m), 6.68 (2H, m), 6.75 (1H, d, J=8Hz), 6.83 (1H, s), 7.04–7.26 (7H, m), 7.33 (1H, d, J=8Hz), 7.57 (1H, d, J=8Hz), 8.30 (1H, m) MS (FAB); m/z 510 (MH$^+$)

Example 28

1-[3-(4-Diethylcarbamoylphenyl)-3-(3-hydroxyphenyl)Propyl]-4-(2-hydroxymethyl-1H-benzimidazol-1-yl)Piperidine Hydrochloride The title compound was obtained in the same manner in Example 1 from 1-bromo-3-(4-diethylcarbamoylphenyl)-3-(3-hydroxyphenyl)propane obtained in the same manner in Reference Example 1 and 4-(2-hydroxymethyl-1H-benzimidazol-1-yl)piperidine trifluoroacetate obtained in the same manner in Reference Example 2. Yield: 58%.

$^1$H-NMR (CDCl$_3$, free base); δ (ppm) 1.06 (3H, br-s), 1.21 (3H, br-s), 1.79 (2H, m), 2.05 (2H, m), 2.21 (2H, m), 2.35 (2H, m), 2.46 (2H, m), 2.96 (1H, m), 3.04 (1H, m), 3.19 (2H, br-s), 3.49 (2H, br-s), 3.84 (1H, m), 4.40 (1H, m), 4.89 (2H, s), 6.77 (3H, m), 7.14 (7H, m), 7.43 (1H, m), 7.68 (1H, m) MS (FAB); m/z 541 (MH$^+$)

Example 29

1-[3-(4-Diethylcarbamoylphenyl)-3-phenylpropyl]-4-(1,3-dihydro-2H-benzimidazol-2-on-1-yl) Piperidine The title compound was obtained in the same manner in Example 1 from 1-bromo-3-(4-diethylcarbamoylphenyl)-3-phenylpropane obtained in the same manner in Reference Example 1 and 4-(1,3-dihydro-2H-benzimidazol-2-on-1-yl) piperidine. Yield: 20%.

$^1$H-NMR (CDCl$_3$); δ (ppm) 1.11 (3H, br-s), 1.24 (3H, br-s), 1.79 (2H, m), 2.11 (2H, m), 2.33 (4H, m), 2.46 (2H, m), 3.04 (2H, m), 3.26 (2H, br-s), 3.53 (2H, br-s), 4.11 (1H, m), 4.35 (1H, m), 7.05 (3H, m), 7.30 (10H, m), 9.97 (1H, s) MS (FAB); m/z 541 (MH$^+$)

Example 30

1-[3-(4-Diisopropylcarbamoylphenyl)-3-(3-methoxyphenyl)Propyl]-4-(1,3-dihydro-2 H-benzimidazol-2-on-1-yl)Piperidine The title compound was obtained in the same manner in Example 1 from 1-bromo-3-(4-diisopropylcarbamoylphenyl)-3-(3-methoxyphenyl)propane obtained in the same manner in Reference Example 1 and 4-(1,3-dihydro-2H-benzimidazol-2-on-1-yl)piperidine. Yield: 48%.

1H-NMR (CDCl$_3$); δ (ppm) 1.26 (6H, br-s), 1.49 (6H, br-s), 1.75 (2H, m), 2.11 (2H, m), 2.27 (2H, m), 2.33 (2H, m), 2.46 (2H, m), 3.04 (2H, m), 3.51 (1H, br-s), 3.79 (3H, s), 4.00 (1H, br-s), 4.13 (1H, m), 4.34 (1H, m), 6.76 (1H, m), 6.83 (1H, s), 6.89 (1H, m), 7.06 (3H, m), 7.25 (6H, m), 9.88 (1H, s) MS (TSP); m/z 569 (MH$^+$)

Example 31

1-[3-(4-Diethylcarbamoylphenyl)-3-(4-fluorophenyl) Propyl]-4-(1,3-dihydro-2H-benzimidazol-2-on-1-yl) Piperidine The title compound was obtained in the same manner in Example 1 from 1-bromo-3-(4-diisopropylcarbamoylphenyl)-3-(4-fluorophenyl)propane obtained in the same manner in Reference Example 1 and 4-(1,3-dihydro-2H-benzimidazol-2-on-1-yl)piperidine. Yield: 37%.

$^1$H-NMR (CDCl$_3$); δ (ppm) 1.12 (3H, br-s), 1.24 (3H, br-s), 1.82 (2H, m), 2.12 (2H, m), 2.28 (4H, m), 2.48 (2H, m), 3.04 (2H, m), 3.26 (2H, br-s), 3.53 (2H, br-s), 4.12 (1H, m), 4.34 (1H, m), 6.99 (2H, m), 7.06 (3H, m), 7.27 (7H, m), 9.96 (1H, s) MS (TSP); m/z 529 (MH$^+$)

Example 32

1-[3-(4-Piperidinocarbonylphenyl)-3-(3-methoxyphenyl)Propyl]-4-(1,3-dihydro-2H-benzimidazol-2-on-1-yl)Piperidine The title compound was obtained in the same manner in Example 1 from 1-bromo-3-(4-piperidinocarbonylphenyl)-

3-(3-methoxyphenyl)propane obtained in the same manner in Reference Example 1 and 4-(1,3-dihydro-2H-benzimidazol-2-on-1-yl)piperidine. Yield: 51%.

$^1$H-NMR (CDCl$_3$); δ (ppm) 1.51 (2H, m), 1.66 (4H, m), 1.80 (2H, m), 2.11 (2H, m), 2.26 (2H, m), 2.33 (2H, m), 2.45 (2H, m), 3.05 (2H, m), 3.34 (2H, br-s), 3.69 (2H, br-s), 3.79 (3H, s), 4.01 (1H, t, J=7Hz), 4.34 (1H, m), 6.75 (1H, m), 6.82 (1H, s), 6.87 (1H, d, J=8Hz), 7.06 (3H, m), 7.23 (1H, t, J=8Hz), 7.31 (5H, m), 9.85 (1H, s) MS (TSP); m/z 553 (MH$^+$)

Example 33

1-[3-(4-Diethylcarbamoylphenyl)-3-(3-hydroxyphenyl)Propyl]-4-(1H-benzimidazol-1-yl) Piperidine Hydrochloride The title compound was obtained in the same manner in Example 2 from the 1-[3-(4-diethylcarbamoylphenyl)-3-(3-methoxyphenyl)propyl]-4-(1H-benzimidazol-1-yl) piperidine obtained in Example 11. Yield: 57%.

$^1$H-NMR (CDCl$_3$, free base); δ (ppm) 1.11 (3H, br-s), 1.24-(3H, br-s), 2.11 (8H, m), 2.35 (2H, m), 3.04 (2H, m), 3.25 (2H, br-s), 3.53 (2H, br-s), 3.93 (1H, m), 4.18 (1H, m), 6.76 (3H, m), 7.27 (8H, m), 7.80 (1H, m), 7.98 (1H, s) MS (TSP); m/z 511 (MH$^+$)

Example 34

1-[3-(4-Carboxylphenyl)-3-(3-methoxyphenyl) Propyl]-4-(1,3-dihydro-2H-benzimidazol-2-on-1-yl) Piperidine Hydrochloride 1-[3-[4-(4,4-Dimethyloxazolin-2-yl)phenyl]-3-(3-methoxyphenyl)propyl]-4-(1,3-dihydro-2H-benzimidazol-2-on-1-yl)piperidine (20.2 mg) was obtained in the same manner in Example 1 from 3-[4-(4,4-dimethyloxazolin-2-yl)phenyl]-1-methanesulfonyloxy-3-(3-methoxyphenyl) propane (61.4 mg) obtained in the same manner in Reference Example 1 and 4-(1,3-dihydro-2H-benzimidazol-2-on-1-yl)piperidine (26.6 mg). Yield: 31%.

The resulting compound (18.6 mg) was dissolved in a mixed solution of dioxane (0.4 ml) and 6 N hydrochloric acid (0.4 ml) and stirred at 100° C. for 5.5 hours. The solvent was evaporated under reduced pressure, and the residue was purified by using LH-20 (elution solvent: dichloromethane:methanol=1:1) to obtain 10 mg of the title compound. Yield: 56%.

$^1$H-NMR (CD$_3$OD); δ (ppm) 2.03 (2H, d, J=14Hz), 2.63 (2H, br-s), 2.84 (2H, m), 3.00–3.25 (4H, m), 3.73 (2H, m), 3.76 (3H, s), 4.13 (1H, t, J=7Hz), 4.53 (1H, m), 6.80 (1H, m), 6.91 (2H, m), 7.05 (3H, s), 7.20–7.40 (2H, m), 7.49 (2H, br-s), 8.00 (2H, br-s) MS (TSP); m/z 486 (MH$^+$)

Example 35

4-(1,3-Dihydro-2H-benzimidazol-2-on-1-yl)-1-[3-(4-methoxycarboxyl-phenyl)-3-(3-methoxyphenyl) Propyl]Piperidine The 1-[3-(4-carboxylphenyl)-3-(3-methoxyphenyl) propyl]-4-(1,3-dihydro-2H-benzimidazol-2-on-1-yl) piperidine hydrochloride (10 mg) obtained in Example 34 was dissolved in methanol (0.5 ml), added with concentrated sulfuric acid (30 μl) and stirred at 65° C. for 5 hours. The reaction mixture was added with saturated aqueous sodium hydrogencarbonate (2 ml) and extracted twice with dichloromethane (2 ml). The organic layer was dried over anhydrous magnesium sulfate, and then the solvent was evaporated under reduced pressure. The residue was purified by preparative thin layer silica gel column chromatography (developing solvent: dichloromethane:methanol=10:1) to obtain 4.2 mg of the title compound. Yield: 44%.

$^1$H-NMR (CDCl$_3$); δ (ppm) 1.81 (2H, d, J=12Hz), 2.11 (2H, t, J=12Hz), 2.33 (4H, m), 2.46 (2H, m), 3.04 (2H, d, J=12Hz), 3.78 (3H, s), 3.89 (3H, s), 4.06 (1H, t, J=7Hz), 4.34 (1H, m), 6.74 (1H, d, J=8Hz), 6.80 (1H, s), 6.85 (1H, d, J=8Hz), 7.00–7.10 (3H, m), 7.20–7.30 (2H, m), 7.34 (2H, d, J=8Hz), 7.95 (2H, d, J=8Hz), 9.06 (1H, br-s) MS (FAB); m/z 500 (MH$^+$)

Example 36

4-Acetyl-1-[3-(4-diethylcarbamoylphenyl)-3-(3-methoxyphenyl)Propyl]-4-phenylpiperidine The title compound was obtained in the same manner in Example 1 from the 1-bromo-3-(4-diethylcarbamoylphenyl)-3-(3-methoxyphenyl)propane obtained in Reference Example 1 and 4-acetyl-4-phenylpiperidine hydrochloride. Yield: 86%.

$^1$H-NMR (CDCl$_3$); δ (ppm) 1.10 (3H, br-s), 1.25 (3H, br-s), 1.89 (3H, s), 2.05 (2H, m), 2.22 (6H, m), 2.46 (2H, m), 2.67 (2H, m), 3.25 (2H, br-s), 3.52 (2H, br-s), 3.77 (3H, s), 3.96 (1H, t, J=7Hz), 6.72 (1H, d, J=8Hz), 6.77 (1H, s), 6.82 (1H, d, J=8Hz), 7.15–7.35 (10H, m) MS (FAB); m/z 527 (MH$^+$)

Example 37

1'-[3-(4-Diethylaminosulfonylphenyl)-3-(3-methoxyphenyl)Propyl]-2,3-dihydro-5-methylspiro [Isoquinoline-4(1H),4'-piperidin]-1-one The title compound was obtained in the same manner in Example 1 from 1-bromo-3-(4-diethylaminosulfonylphenyl)-3-(3-methoxyphenyl)propane obtained in the same manner in Reference Example 1 and the 2,3-dihydro-5-methylspiro-[isoquinoline-4(1H),4'-piperidin]-1-one trifluoroacetate obtained in Reference Example 3. Yield: 67%.

$^1$H-NMR (CDCl$_3$); δ (ppm) 1.12 (6H, t, J=7Hz), 1.72 (2H, d, J=14Hz), 2.13 (2H, t, J=14Hz), 2.25 (4H, m), 2.60 (2H, m), 2.67 (3H, s), 2.78 (2H, m), 3.21 (4H, q, J=7Hz), 3.52 (2H, s), 3.78 (3H, s), 4.06 (1H, m), 5.85 (1H, br-s), 6.76 (2H, m), 6.83 (1H, d, J=8Hz), 7.20–7.35 (3H, m), 7.37 (2H, d, J=8Hz), 7.71 (2H, d, J=8Hz), 8.03 (1H, d, J=8Hz) MS (EI); m/z 589 (M$^+$)

Example 38

2,3-Dihydro-5-methyl-1'-[3-[4-(1-methylbutyryl) Phenyl]-3-(3-methoxyphenyl)Propyl]Spiro [Isoquinoline-4(1H),4'-piperidin]-1-one The title compound was obtained in the same manner in Example 1 from 1-bromo-3-(3-methoxyphenyl)-3-[4-(1-methylbutyryl)phenyl]propane obtained in similar manner to that of Reference Example 1 and the 2,3-dihydro-5-methylspiro-[isoquinoline-4(1H),4'-piperidin]-1-one trifluoroacetate obtained in Reference Example 3. Yield: 51%.

$^1$H-NMR (CDCl$_3$); δ (ppm) 0.90 (3H, t, J=7Hz), 1.16 (3H, d, J=7Hz), 1.47 (1H, m), 1.72 (2H, d, J=14Hz), 1.79 (1H, m), 2.17 (2H, t, J=14Hz), 2.29 (4H, m), 2.58 (2H, m), 2.63 (3H, s), 2.80 (2H, m), 3.35 (1H, m), 3.52 (2H, s), 3.78 (3H, s), 4.05 (1H, t, J=7Hz), 6.30 (1H, br-s), 6.74 (1H, d, J=8Hz), 6.80 (1H, s), 6.85 (1H, d, J=8Hz), 7.15–7.30 (3H, m), 7.35 (2H, d, J=8Hz), 7.87 (2H, d, J=8Hz), 8.02 (1H, d, J=8Hz) MS (EI); m/z 538 (M⁺)

Example 39

1-[3-(4-Diethylaminomethylphenyl)-3-(3-methoxyphenyl)Propyl]-4-(1H-benzimidazol-1-yl) Piperidine A suspension of lithium aluminum hydride (9.7 mg) in tetrahydrofuran (0.3 ml) was added with a solution of the 1-[3-(4-diethylcarbamoylphenyl)-3-(3-methoxy-phenyl)propyl]-4-(1H-benzimidazol-1-yl)piperidine (67.1 mg) obtained in Example 11 dissolved in toluene (1.2 ml) and stirred at room temperature for 18 hours. The reaction mixture was added with one drop of water and one drop of 5 N aqueous sodium hydroxide and further stirred at room temperature for 1 hour. The reaction mixture was added with anhydrous magnesium sulfate and filtered, and then the solvent was evaporated under reduced pressure to obtain 64.9 mg of the title compound. Yield: 99%.

$^1$H-NMR (CDCl$_3$); δ (ppm) 1.03 (6H, t, J=7Hz), 2.14 (6H, m), 2.25 (2H, m), 2.36 (2H, m), 2.50 (4H, q, J=7Hz), 3.07 (2H, m), 3.54 (2H, s), 3.77 (3H, s), 3.97 (1H, t, J=7Hz), 4.17 (1H, m), 6.72 (1H, d, J=8Hz), 6.81 (1H, s), 6.87 (1H, d, J=8Hz), 7.15–7.30 (7H, m), 7.42 (1H, m), 7.81 (1H, m), 8.03 (1H, s) MS (EI); m/z 510 (M⁺)

Test Example 1

Binding Affinity for Opioid δ Receptor

A membrane fraction of opioid δ receptor was prepared from the rat forebrain. For the preparation of the membrane fraction, the rat forebrain was homogenized in a 10-fold volume of 0.32 M sucrose solution, and the resulting homogenate was centrifuged at 900×g for 10 minutes. Subsequently, the supernatant was centrifuged at 11,500×g for 20 minutes to obtain precipitates. The precipitates were washed with an assay buffer (50 mM Tris-HCl, pH 7.4) by centrifugation, and the finally obtained membrane fraction was used for the experiment.

A binding experiment was performed by using the resulting membrane fraction and a radioactive ligand [$^3$H]-Naltrindole. In the presence of a test compound, the membrane fraction and [$^3$H]-Naltrindole at a final concentration of 1 nM were added and incubated at 25° C. for 90 minutes. The membrane fraction mixture was rapidly filtered through a GF/B filter to quench the reaction and further washed with the assay buffer (5 ml). The radioactivity was measured by a liquid scintillation counter. Amount of non-specific bindings was determined by using 10 μM Naltrindole, and amount of specific bindings was calculated from the difference of the amounts of measured bindings and the non-specific bindings. IC$_{50}$ value of each compound was determined by nonlinear least square regression analysis, and Ki value was calculated by using the Cheng-Prusoff equation.

The results of the measurement of opioid δ receptor binding affinity of the compounds of the present invention by the above method are shown in Table 1 below.

TABLE 1

|  | Binding affinity Ki (nM) |
| --- | --- |
| Compound of Example 4 | 345 |
| Compound of Example 9 | 1212 |
| Compound of Example 21 | 821 |
| Compound of Example 22 | 171 |

TABLE 1-continued

|  | Binding affinity Ki (nM) |
| --- | --- |
| Compound of Example 23 | 1545 |
| Compound of Example 32 | 2762 |

Industrial Applicability

The compounds of the present invention have effective and selective affinity for opioid δ receptors and are useful as active ingredients of medicaments for therapeutic or preventive treatment of central nerve system diseases including schizophrenia, depression, cerebral apoplexy, epilepsy, Alzheimer's disease and Parkinson's disease and peripheral nerve system diseases including pains.

What is claimed is:

1. A compound represented by the following general formula (I) or a salt thereof:

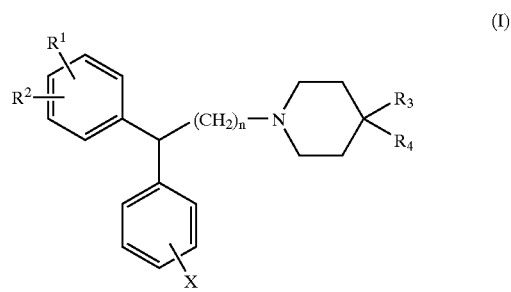

(I)

wherein, X represents the following group (II), (III), (IV), (V), or (VI),

(II)

(III)

(IV)

(V)

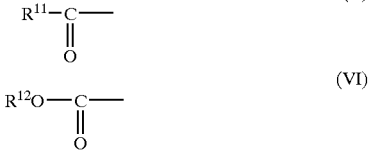

(VI)

n represents 1, 2 or 3,

R$^1$ and R$^2$ each independently represent a hydrogen atom, a halogen atom, a lower alkyl group which may be substituted, a lower alkenyl group which may be substituted, a lower alkoxy group which may be substituted or a hydroxy group, or R$^1$ and R$^2$ are combined to form the group —O—CH$_2$—O—, R$^3$ represents a hydrogen atom, a halogen atom, a lower alkyl group which may be substituted, a lower alkenyl group which may be substituted, a lower alkoxy group which may be substituted, a hydroxy group, a cyano group, an amino group which may be substituted, a carbamoyl group which may be substituted, a carboxyl group, a (substituted or unsubstituted lower alkoxy) carbonyl group or a (substituted or unsubstituted lower alkyl)carbonyl group, $R^4$ represents a saturated or unsaturated monocyclic or bicyclic carbocyclic group or a monocyclic or bicyclic heterocyclic group containing one or more hetero atoms selected from an oxygen atom, a nitrogen atom, and a sulfur atom, $R^5$, $R^6$, $R^7$, $R^8$, $R^9$, $R^{10}$, $R^{11}$, and $R^{12}$ each independently represent a hydrogen atom, a lower alkyl group which may be substituted, or a lower alkenyl group which may be substituted, and $R^3$ and $R^4$, $R^5$ and $R^6$, $R^7$ and $R^8$, or $R^9$ and $R^{10}$ may be linked to each other to form a cyclic structure.

2. The compound or a salt thereof according to claim 1, wherein $R^4$ represents a residue of a benzene, indole, or a benzimidazole ring, wherein a part of unsaturated bonds of said ring may be hydrogenated to form a saturated bond(s), or the ring may be substituted.

3. The compound or a salt thereof according to claim 1, wherein $R^3$ and $R^4$ are combined to form the following group (VII) or (VIII):

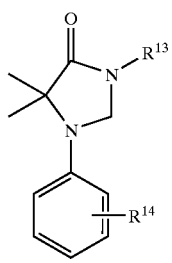

(VII)

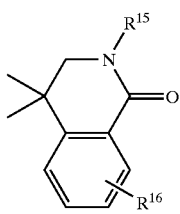

(VIII)

wherein, $R^{13}$ and $R^{15}$ each independently represent a hydrogen atom, a lower alkyl group which may be substituted, or a lower alkenyl group which may be substituted, and $R^{14}$ and $R^{16}$ each independently represent a hydrogen atom, a halogen atom, a lower alkyl group which may be substituted, a lower alkenyl group which may be substituted, a lower alkoxy group which may be substituted, a hydroxy group, a cyano group, an amino group which may be substituted, a nitro group, a carbamoyl group which may be substituted, a carboxyl group, a (substituted or unsubstituted lower alkoxy) carbonyl group or a (substituted or unsubstituted lower alkyl)carbonyl group.

4. The compound or a salt thereof according to any one of claim 1, wherein X represents the group (II), (III), (V) or (VI), n represents 2 or 3, $R^1$ and $R^2$ each independently represent a hydrogen atom, a halogen atom, a lower alkoxy group or a hydroxy group, or $R^1$ and $R^2$ represent —O—CH$_2$—O—

$R^3$ represents a hydrogen atom or a lower alkylcarbonyl group, $R^4$ represents a residue of a benzene, indole and benzimidazole ring wherein a part of the unsaturated bonds of the ring may be hydrogenated to form a saturated bond(s), and a hydrogen atom on the ring may be substituted with an oxo group, a lower alkyl group, a hydroxymethyl group, or a benzyl group, or $R^3$ and $R^4$ are combined to form a cyclic structure selected from an imidazole, N-phenylimidazolidine, and an isoquinoline ring wherein the ring may be substituted with an oxo group or a lower alkyl group, and $R^5$, $R^6$, $R^7$, $R^8$, $R^9$, $R^{10}$, $R^{11}$, and $R^{12}$ each independently represent a hydrogen atom or a lower alkyl group, or $R^5$ and $R^6$ are combined to form a piperidine ring.

5. The compound or a salt thereof according to any one of claim 1, wherein X represents the group (II).

6. The compound or a salt thereof according to claim 2, wherein X represents the group (II).

7. The compound or a salt thereof according to claim 3, wherein X represents the group (II).

8. The compound or a salt thereof according to claim 4, wherein X represents the group (II).

9. The compound or a salt thereof according to claim 1, wherein the compound or salt acts on an opioid δ receptor.

10. A pharmaceutical composition, wherein the composition comprises at least one of a compound of general formula (I) according to claim 1 and a pharmacologically acceptable salt thereof as an active ingredient.

11. The pharmaceutical composition according to claim 10, wherein the composition further comprises one or more pharmaceutical additives.

12. The pharmaceutical composition according to claim 10, wherein the composition has an affinity for an opioid δ receptor.

13. The pharmaceutical composition according to claim 10, wherein the composition is used for the treatment of at least one of depression, epilepsy and Parkinson's disease.

14. The pharmaceutical composition according to claim 10, wherein the composition is used for the treatment of pain.

15. A method for the treatment of at least one of depression, epilepsy and Parkinson's disease, wherein the method comprises the administration of a therapeutically effective amount of at least one of a compound according to claim 1 and a pharmacologically acceptable salt thereof to a mammal.

16. The method according to claim 15, wherein the mammal is a human.

17. A method for the treatment of pain, wherein the method comprises the administration of a therapeutically effective amount of at least one of a compound according to claim 1 and a pharmacologically acceptable salt thereof to a mammal.

18. The method according to claim 17, wherein the mammal is a human.

19. The compound or a salt thereof according to claim 1, wherein X represents the group (II), (III), (V) or (VI), n represents 2 or 3, $R^1$ and $R^2$ each independently represent a hydrogen atom, a halogen atom, a lower alkoxy group or a hydroxy group, or $R^1$ and $R^2$ together represent —O—CH$_2$—O—, $R^3$ represents a hydrogen atom or a lower alkylcarbonyl group, $R^4$ represents a residue of a benzene, an indole, or a benzimidazole ring, wherein a part of the unsaturated bonds of said ring may be hydrogenated to form one or more saturated bonds, and the ring may be substituted; and $R^5$, $R^6$, $R^7$, $R^8$, $R^9$, $R^{10}$, $R^{11}$, and $R^{12}$ each independently represent a hydrogen atom or a lower alkyl group, or $R^5$ and $R^6$ are combined to form a piperidine ring.

20. The compound or a salt thereof according to claim 1, wherein X represents the group (II), (III), (V) or (VI), n represents 2 or 3, $R^1$ and $R^2$ each independently represent a hydrogen atom, a halogen atom, a lower alkoxy group or a hydroxy group, or $R^1$ and $R^2$ together represent —O—CH$_2$—O—, $R^3$ and $R^4$ are combined to form a cyclic structure selected from an imidazole, an N-phenylimidazolidine, and an isoquinoline ring wherein the ring may be substituted with an oxo group or a lower alkyl group; and $R^5$, $R^6$, $R^7$, $R^8$, $R^9$, $R^{10}$, $R^{11}$, and $R^{12}$ each independently represent a hydrogen atom or a lower alkyl group, or $R^5$ and $R^6$ are combined to form a piperidine ring.

\* \* \* \* \*

UNITED STATES PATENT AND TRADEMARK OFFICE
CERTIFICATE OF CORRECTION

PATENT NO. : 6,790,854 B2
DATED : September 14, 2004
INVENTOR(S) : M. Tsushima et al.

It is certified that error appears in the above-identified patent and that said Letters Patent is hereby corrected as shown below:

Title page,
Item [56], References Cited, FOREIGN PATENT DOCUMENTS, insert
-- 01/60796   08/23/01   W.I.P.O.
   1256575   11/13/02   E.P.O. --

Column 28,
Line 18, before "general" delete "following".
Line 33, after "wherein" delete ",".
Line 33, after "represents" insert -- one of --.
Line 33, "group" should be -- groups --.

Column 29,
Line 21, after "part of" insert -- the --.
Line 22, "form a saturated bond(s), or the" should be -- form one or more saturated bonds, and the --.
Line 25, "group" should be -- groups --.
Line 61, before "claim 1" delete "any one of".
Line 67, before "represent" insert -- together --.

Column 30,
Line 3, "indole and benzimidazole" should be -- an indole or a benzimidazole --.
Lines 5-6, "a saturated bond(s)" should be -- one or more saturated bonds --.
Line 10, after "imidazole" insert -- an --.
Line 17, after "to" delete "any one of".

Signed and Sealed this

Seventeenth Day of May, 2005

JON W. DUDAS
*Director of the United States Patent and Trademark Office*